(12) United States Patent
Sperling

(10) Patent No.: US 11,612,489 B2
(45) Date of Patent: *Mar. 28, 2023

(54) METHOD FOR MODELING HUMERAL ANATOMY AND OPTIMIZATION OF COMPONENT DESIGN

(71) Applicant: Mayo Foundation for Medical Education and Research, Rochester, MN (US)

(72) Inventor: John W. Sperling, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/489,335

(22) Filed: Sep. 29, 2021

(65) Prior Publication Data
US 2022/0015915 A1  Jan. 20, 2022

Related U.S. Application Data

(63) Continuation of application No. 16/154,016, filed on Oct. 8, 2018, now Pat. No. 11,229,524, which is a
(Continued)

(51) Int. Cl.
*A61F 2/40* (2006.01)
*B33Y 80/00* (2015.01)
(Continued)

(52) U.S. Cl.
CPC ........ *A61F 2/4059* (2013.01); *A61F 2/30771* (2013.01); *A61F 2/30942* (2013.01); *A61F 2/4003* (2013.01); *B22F 10/20* (2021.01); *B33Y 80/00* (2014.12); *G16H 30/20* (2018.01); *A61F 2002/3093* (2013.01);
(Continued)

(58) Field of Classification Search
CPC .... A61F 2/40; A61F 2/4059; A61F 2002/407; A61F 2002/40762; A61F 2002/4003; A61F 2002/30784
See application file for complete search history.

(56) References Cited

U.S. PATENT DOCUMENTS

| 4,919,670 A | 4/1990 | Dale et al. |
| 5,163,962 A | 11/1992 | Salzstein et al. |

(Continued)

FOREIGN PATENT DOCUMENTS

WO  2016/113563 A1  7/2016

OTHER PUBLICATIONS

International Search Report and Written Opinion from parent international application No. PCT/US2018/024044, dated Jul. 26, 2018, 20 pages.
(Continued)

*Primary Examiner* — Bruce E Snow
(74) *Attorney, Agent, or Firm* — Quarles and Brady LLP

(57) ABSTRACT

Stemless components and fracture stems for joint arthroplasty, such as shoulder arthroplasty, are disclosed. Also, methods and devices are disclosed for the optimization of shoulder arthroplasty component design through the use of medical imaging data, such as computed tomography scan data.

23 Claims, 30 Drawing Sheets

Related U.S. Application Data continuation of application No. PCT/US2018/024044, filed on Mar. 23, 2018.

(60) Provisional application No. 62/476,214, filed on Mar. 24, 2017.

(51) Int. Cl.
    *B22F 10/20* (2021.01)
    *G16H 30/20* (2018.01)
    *A61F 2/30* (2006.01)

(52) U.S. Cl.
    CPC ......... *A61F 2002/30171* (2013.01); *A61F 2002/30332* (2013.01); *A61F 2002/30604* (2013.01); *A61F 2002/30616* (2013.01); *A61F 2002/30784* (2013.01); *A61F 2002/30884* (2013.01); *A61F 2002/30943* (2013.01); *A61F 2002/30948* (2013.01); *A61F 2002/30963* (2013.01); *A61F 2002/4007* (2013.01); *A61F 2002/4062* (2013.01); *A61F 2002/4066* (2013.01)

(56) References Cited

U.S. PATENT DOCUMENTS

| | | | |
|---|---|---|---|
| 5,755,811 A | 5/1998 | Tanamal et al. | |
| 6,217,620 B1 | 4/2001 | Park | |
| 6,530,957 B1 | 3/2003 | Jack | |
| 6,613,093 B2 | 9/2003 | DeCarlo, Jr. et al. | |
| 6,641,616 B1 | 11/2003 | Grundei | |
| 6,749,639 B2 | 6/2004 | Lewallen | |
| 6,887,278 B2 | 5/2005 | Lewallen | |
| 8,062,378 B2 | 11/2011 | Fonte | |
| 8,506,638 B2 | 8/2013 | Vanasse et al. | |
| 8,545,511 B2 | 10/2013 | Splieth et al. | |
| 8,876,908 B2 | 11/2014 | Katrana et al. | |
| 8,926,707 B2 | 1/2015 | McMinn | |
| 9,278,413 B2 | 3/2016 | Sperling | |
| 9,468,502 B2 | 10/2016 | Wiebe, III et al. | |
| 10,603,056 B2 | 3/2020 | Wiebe, III et al. | |
| 11,229,524 B2 * | 1/2022 | Sperling | A61F 2/4003 |
| 2003/0055507 A1 | 3/2003 | McDevitt et al. | |
| 2005/0090902 A1 | 4/2005 | Masini | |
| 2006/0241775 A1 | 10/2006 | Buss | |
| 2007/0173945 A1 | 7/2007 | Wiley et al. | |
| 2009/0118837 A1 | 5/2009 | Winslow et al. | |
| 2009/0177282 A1 | 7/2009 | Bureau et al. | |
| 2009/0265010 A1 | 10/2009 | Anginbaud et al. | |
| 2010/0114326 A1 * | 5/2010 | Winslow | A61F 2/3601 623/23.42 |
| 2010/0274359 A1 * | 10/2010 | Brunnarius | A61F 2/30734 623/19.13 |
| 2011/0029089 A1 | 2/2011 | Giuliani et al. | |
| 2011/0202140 A1 | 8/2011 | Turner et al. | |
| 2012/0010720 A1 | 1/2012 | Dickerson | |
| 2012/0078375 A1 | 3/2012 | Smith et al. | |
| 2012/0130505 A1 | 5/2012 | Long | |
| 2014/0031946 A1 | 1/2014 | Katrana et al. | |
| 2014/0066937 A1 | 3/2014 | Wiebe, III et al. | |
| 2015/0190237 A1 | 7/2015 | Bonin, Jr. et al. | |
| 2015/0223900 A1 | 8/2015 | Wiebe, III et al. | |
| 2015/0223941 A1 | 8/2015 | Lang | |
| 2016/0206436 A1 | 7/2016 | Chavarria et al. | |
| 2017/0007331 A1 | 1/2017 | Couture et al. | |
| 2020/0237385 A1 | 7/2020 | Wiebe, III et al. | |

OTHER PUBLICATIONS

Zimmer—Zimmer Anatomical Shoulder Fracture System (2007).
Zimmer—Anatomical Shoulder Fracture System Surgical Technique (2010).
Biomet—Comprehensive Nano Stemless Shoulder Anatomic and Reverse Surgical Technique (2012).

* cited by examiner

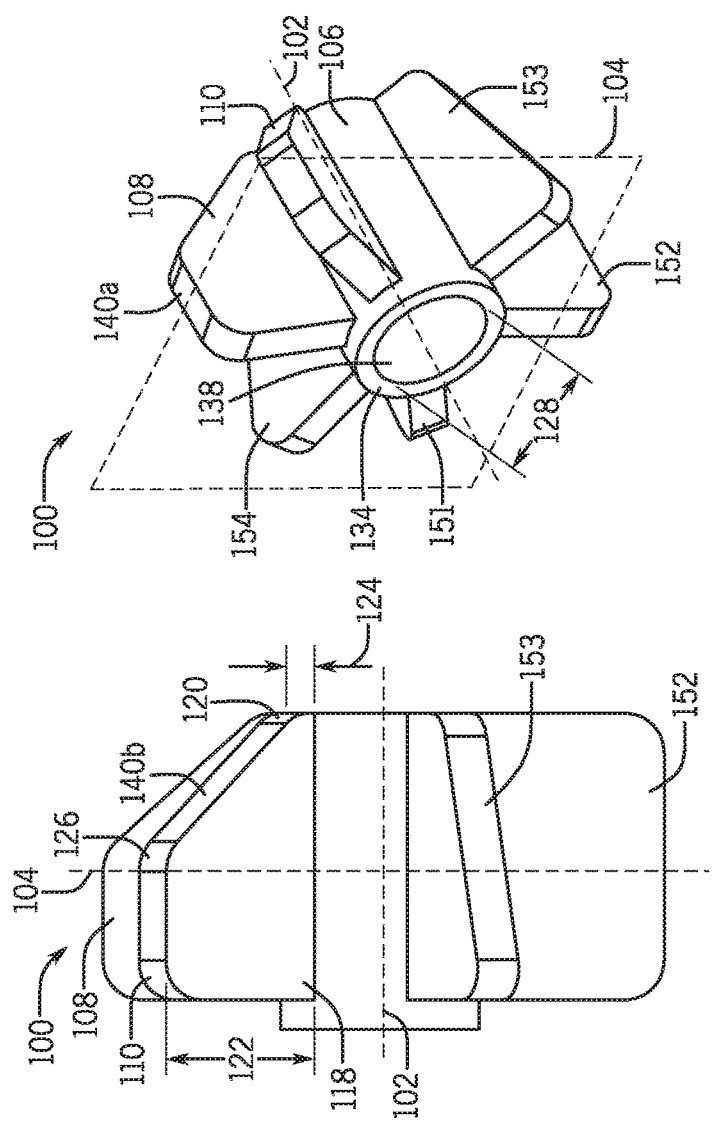
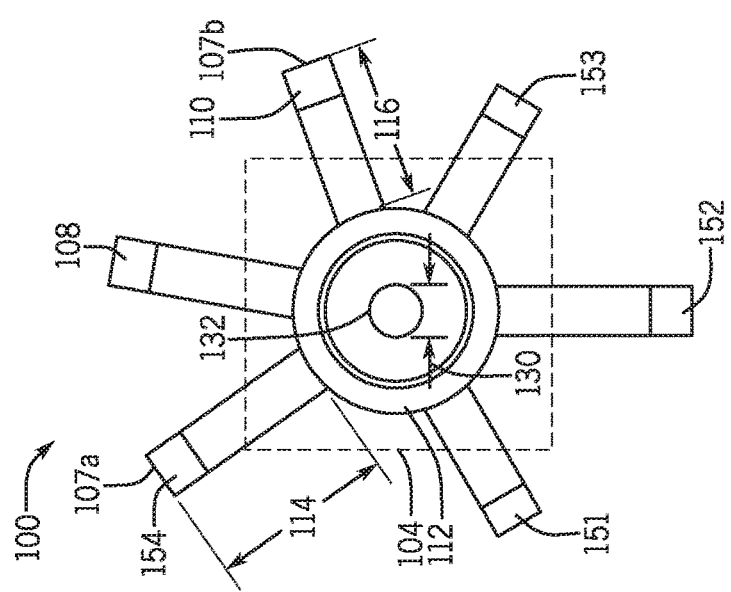
FIG. 3C
FIG. 3B
FIG. 3A

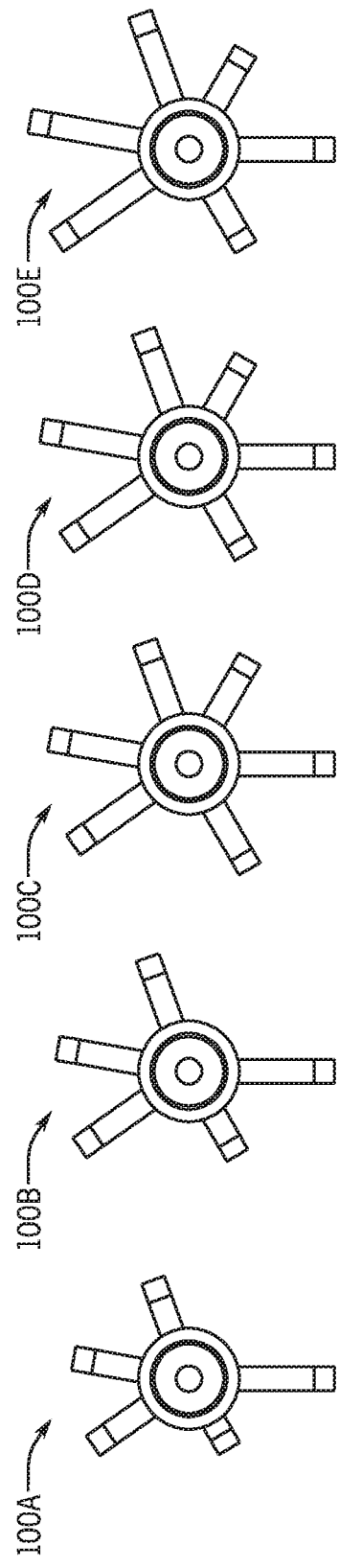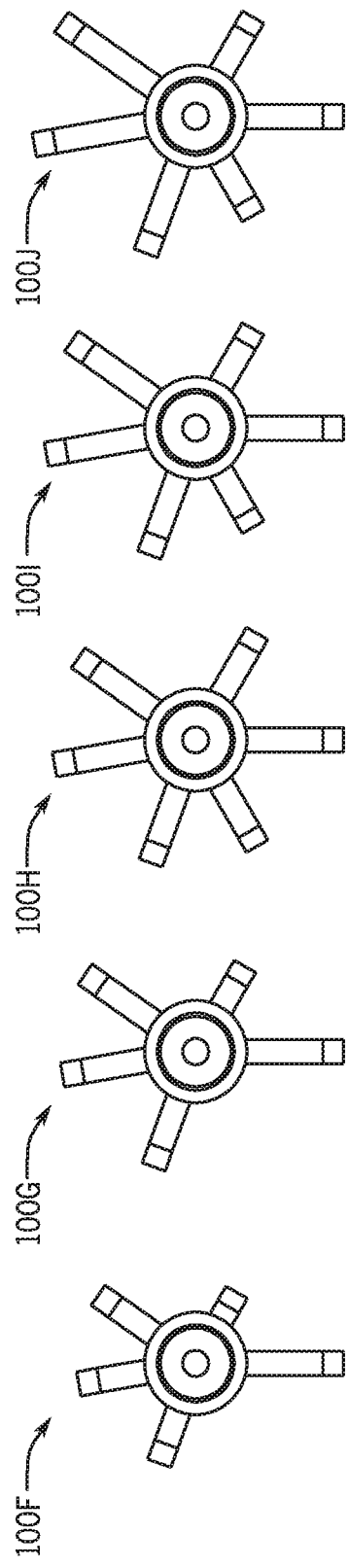

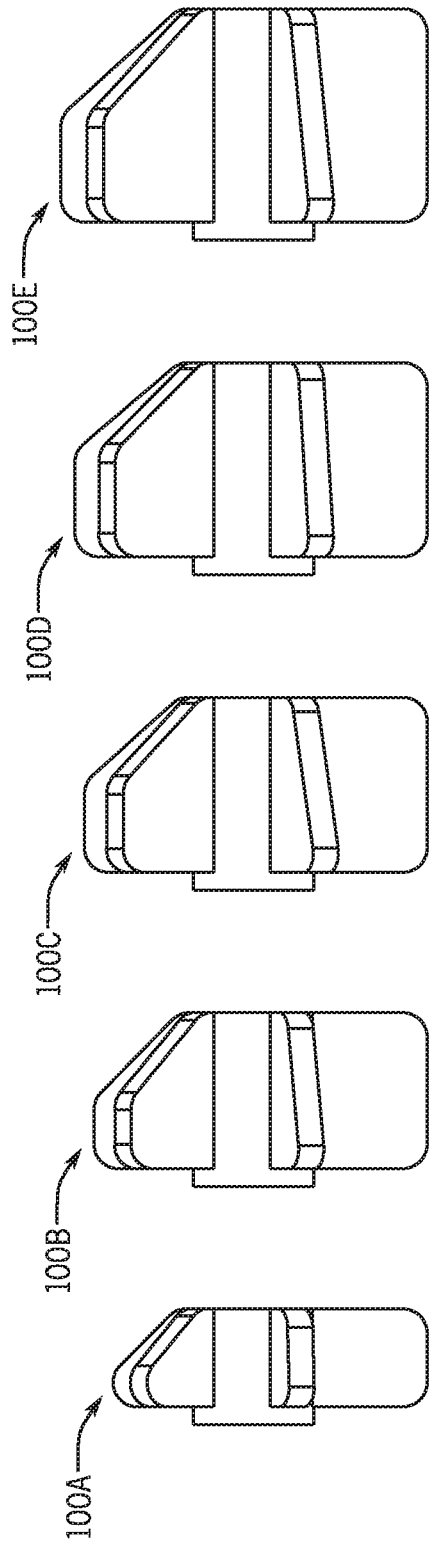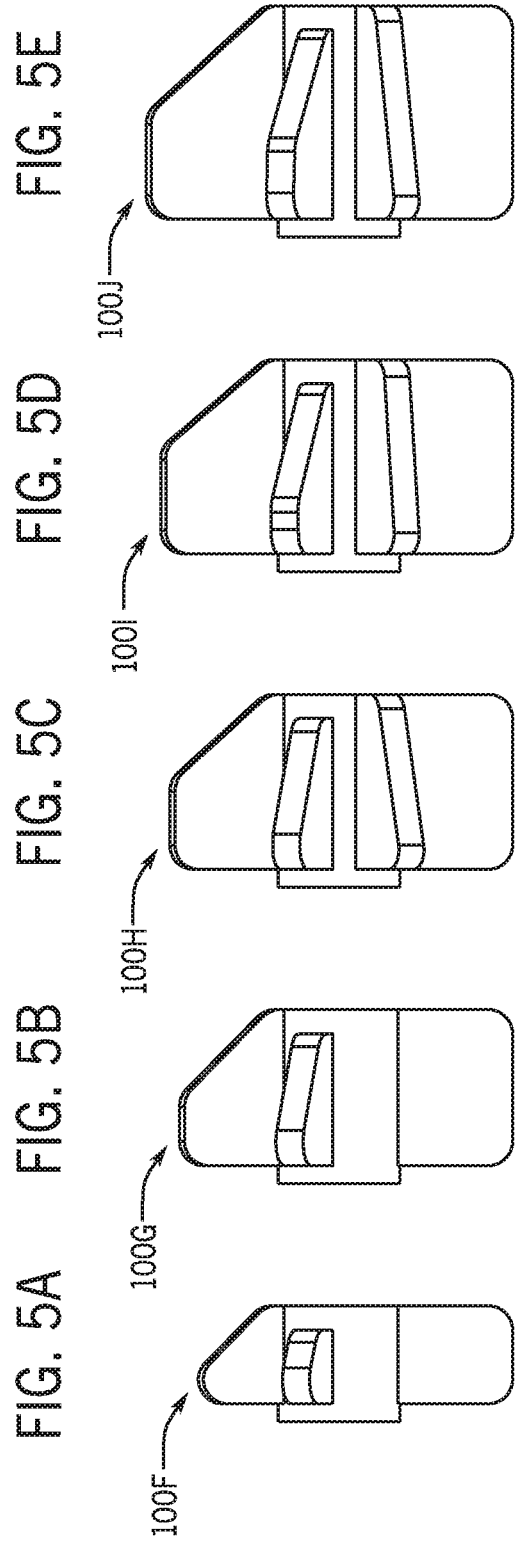

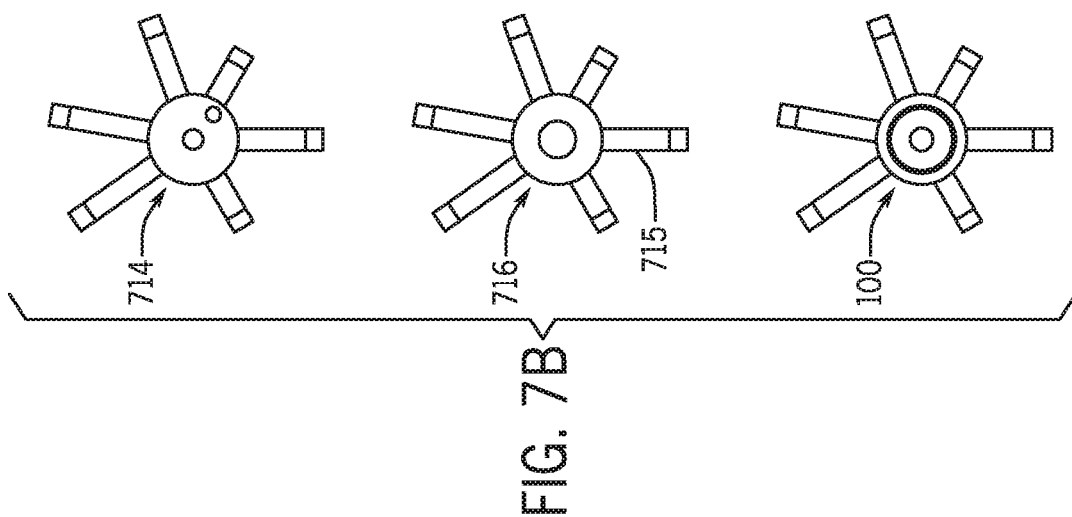
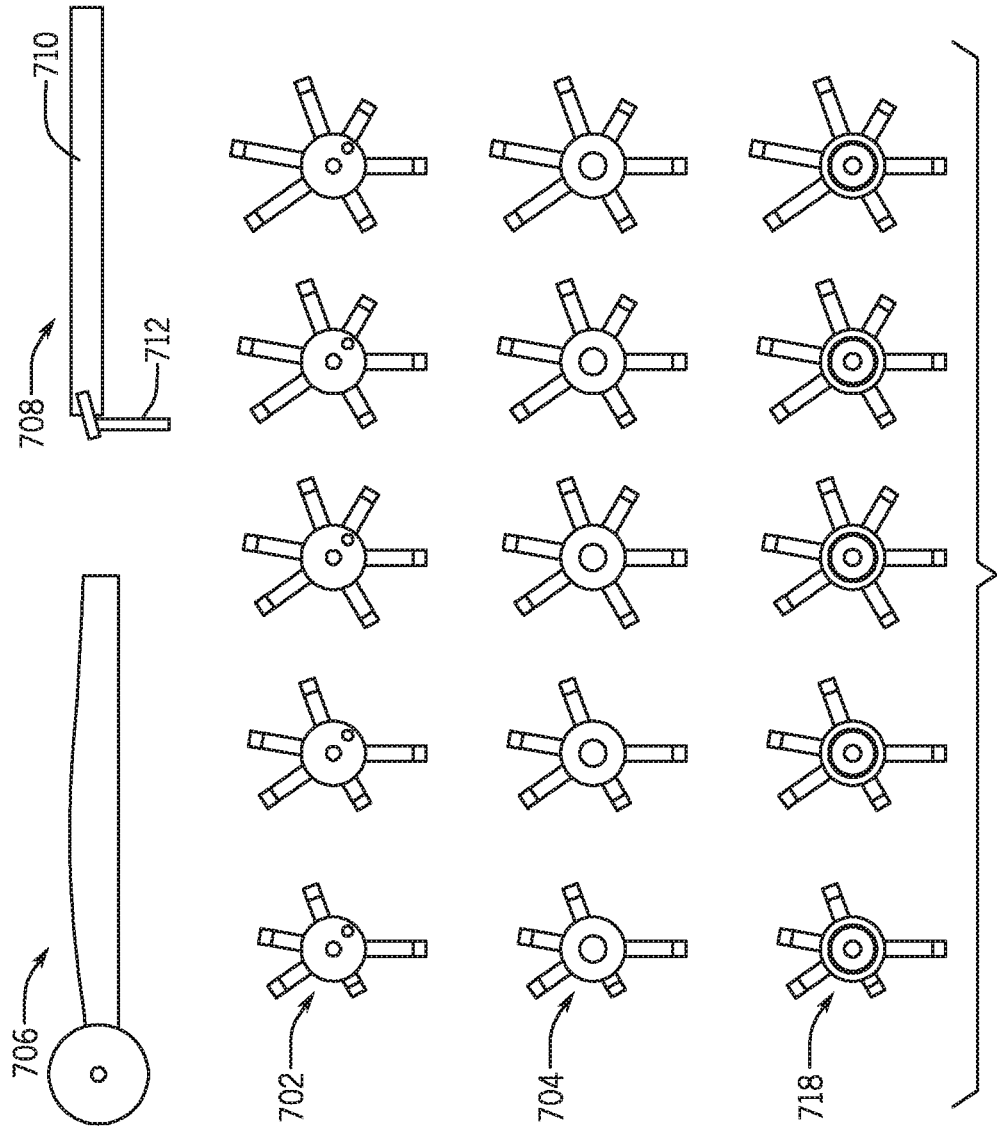

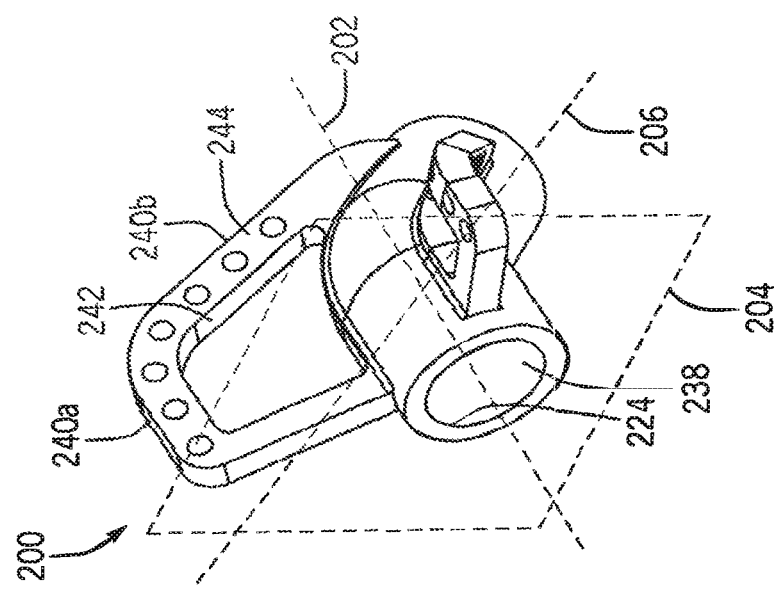
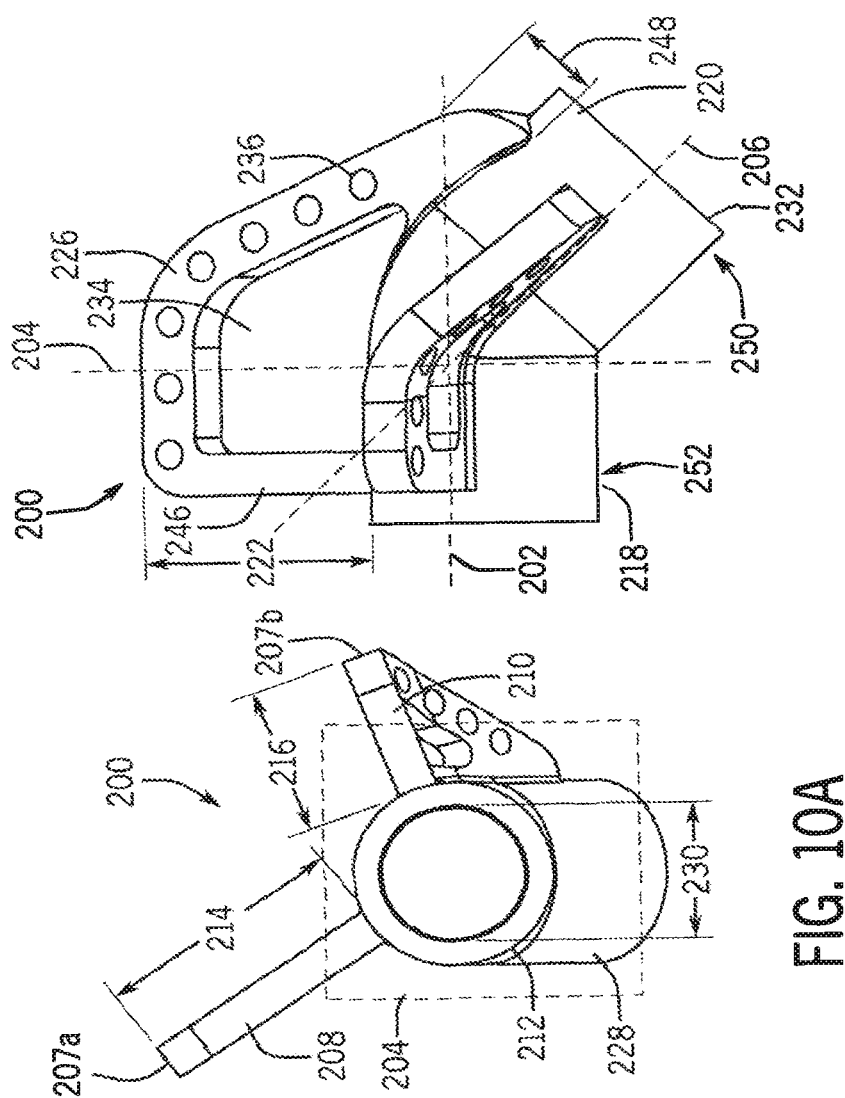
FIG. 10C
FIG. 10B
FIG. 10A

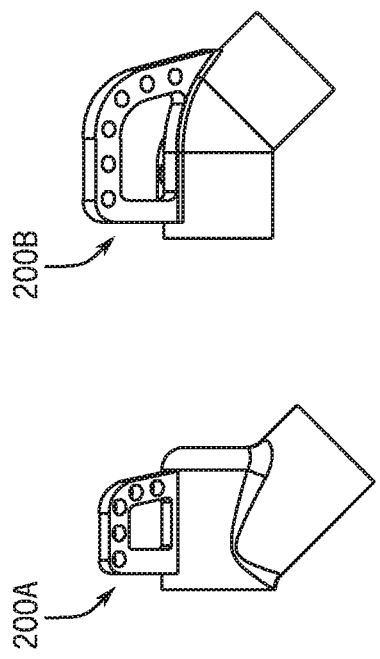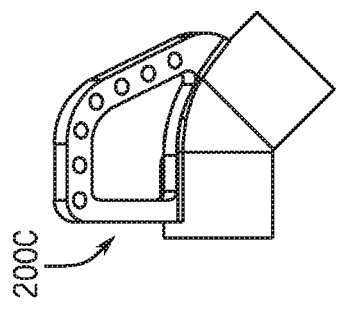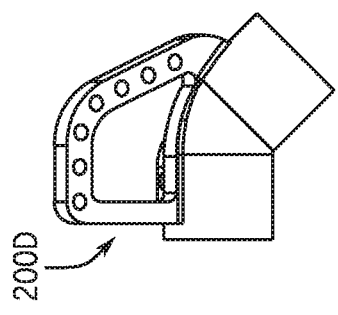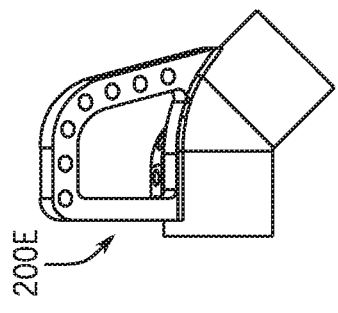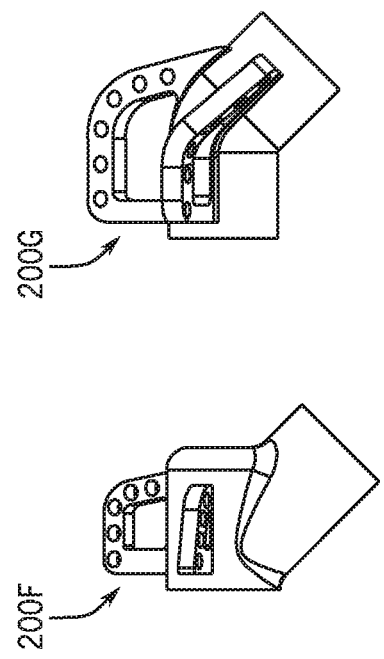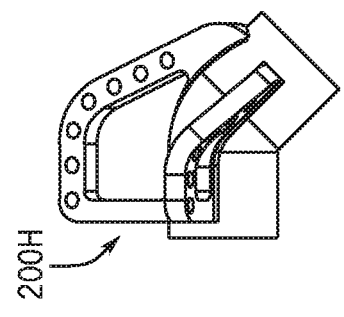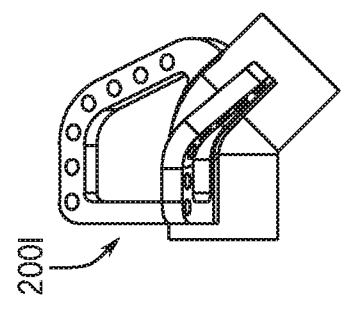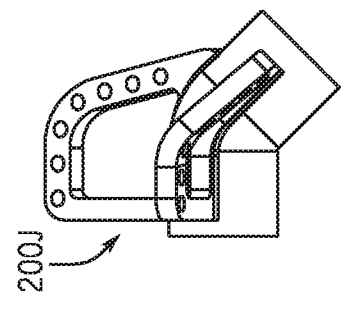

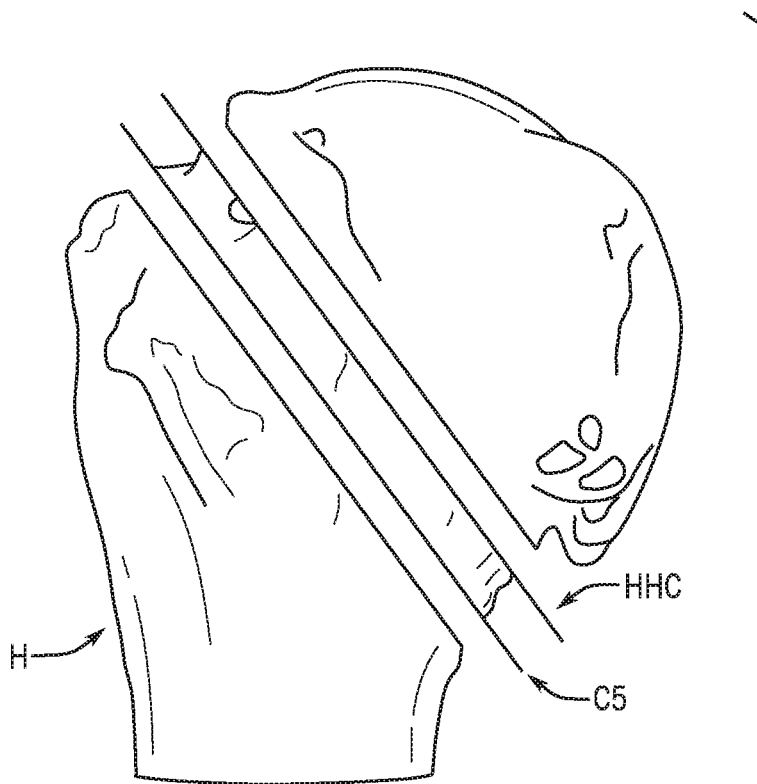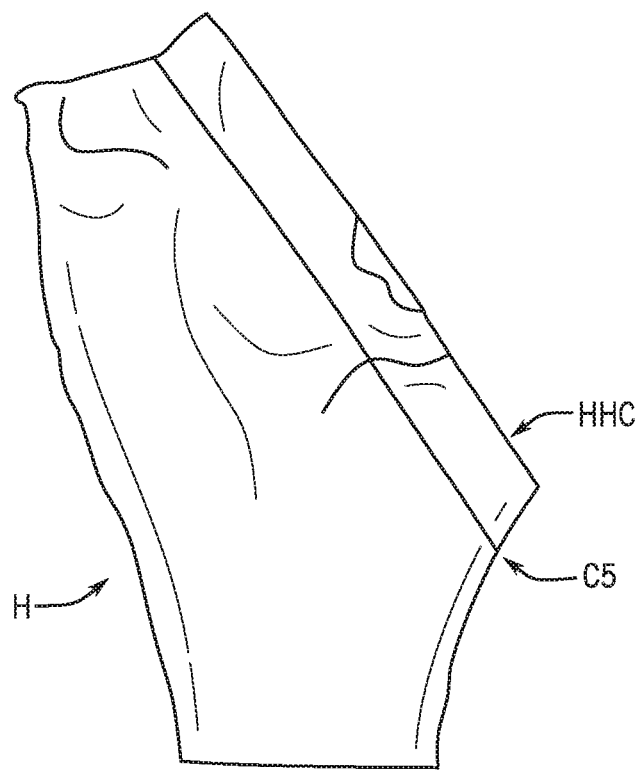
FIG. 23

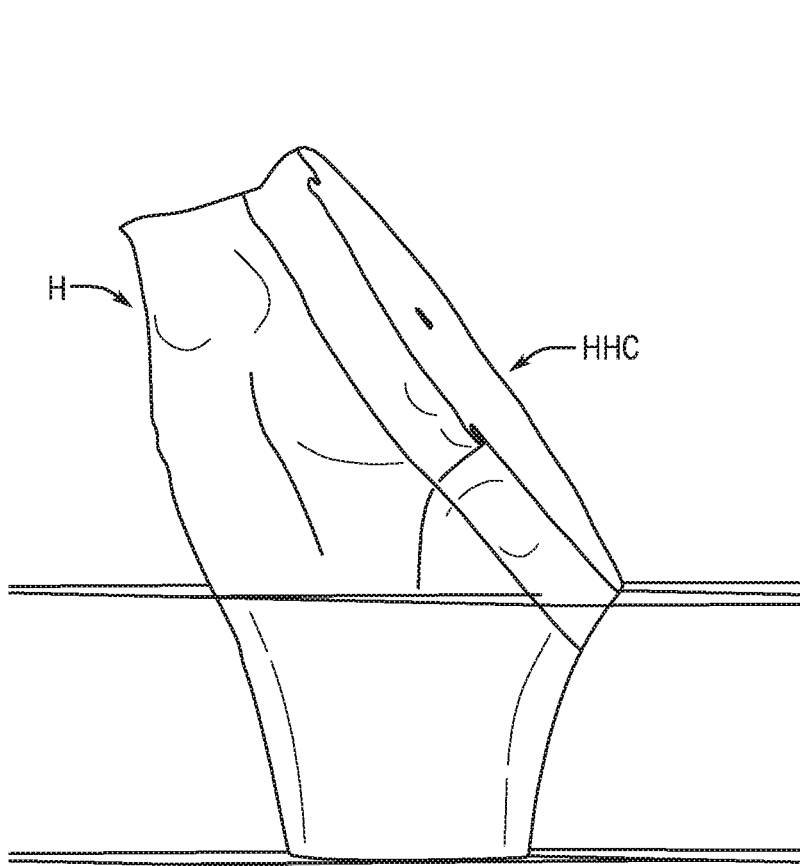
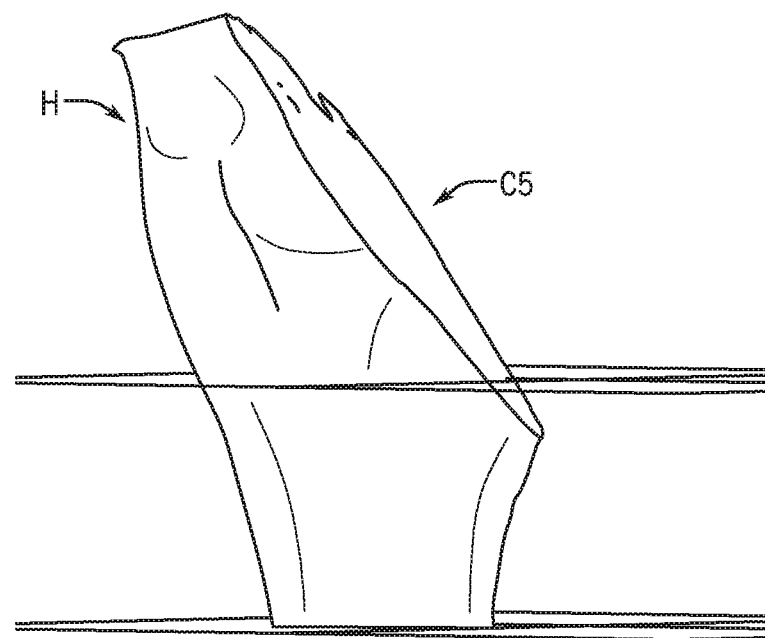
FIG. 27

METHOD FOR MODELING HUMERAL ANATOMY AND OPTIMIZATION OF COMPONENT DESIGN

CROSS-REFERENCES TO RELATED APPLICATIONS

This application is a continuation of U.S. patent application Ser. No. 16/154,016, filed Oct. 8, 2018, which is a continuation application of PCT International Application No. PCT/US18/24044 having an international filing date of Mar. 23, 2018 which claims priority to U.S. Patent Application No. 62/476,214 filed Mar. 24, 2017.

STATEMENT REGARDING FEDERALLY SPONSORED RESEARCH

Not Applicable.

BACKGROUND OF THE INVENTION

1. Field of the Invention

The invention relates to methods for the optimization of joint arthroplasty component design and shoulder arthroplasty components such as stemless components and fracture stems for joint arthroplasty.

2. Description of the Related Art

Various prostheses for the replacement of the shoulder joint are known. In one example shoulder prosthesis, the upper portion of the humerus is replaced by a humeral component including (i) a stem, or cleat, that extends into a bore formed within the humerus and (ii) a generally hemispherical head portion that is connected to the stem. The hemispherical head of the humeral component articulates with a complementary concave section of a glenoid component mounted within the glenoid cavity of the scapula. This type of shoulder prosthesis may be called a "primary" or "total" prosthesis. In another example shoulder prosthesis, often called a hemiarthroplasty, a hemispherical head of the humeral component articulates with the native glenoid. In another example shoulder prosthesis, often called a "reverse" or "inverted" prosthesis, the glenoid component includes a convex section that articulates with a complementary concave proximal section of the head of the humeral component.

There is a breadth of complications in shoulder surgery associated with devices that are not anatomically correct. This includes fracturing the humerus when trying to implant a device that is not in the shape of the humeral anatomy, catastrophic early component loosening when contact with native bone is not optimized, as well as lack of long term bone ingrowth. In addition, a high rate of stress shielding with associated bone resorption has been reported in the literature due to a lack of uniform stress distribution. In the fracture setting, tuberosity resorption remains a significant problem and has a substantial negative impact on patient outcomes.

Thus, there exists a need for improved stemless components and fracture stems for joint arthroplasty, such as shoulder arthroplasty.

SUMMARY OF THE INVENTION

The present invention provides a methodology that improves the understanding of proximal humeral anatomy through the use of CT scan data and 3D modeling. This methodology describes the interaction of anatomical features of the proximal humerus and how these features change based on the specific location in the proximal humerus. Additionally, the methodology has demonstrated that the shape of the proximal humeral region is side specific. Therefore, having right and left specific devices with an anatomic shape in a true population based distribution further facilitates and improves joint prosthetic component design. The methodology can optimize loading and fit at the bone-device interface. Furthermore, models were created to test the methodology and the interaction of the anatomic features and their interdependence on each other. The results of the biomechanical testing validated the methodology demonstrating significantly improved initial fixation compared to currently available standard circular prosthetic component designs. The methodology has also resulted in improved stemless components and fracture stems for joint arthroplasty. The fracture stems include specific features for an improved anatomic fracture fixation device with optimal shape and size of fins to maximize tuberosity healing. Furthermore, cadaveric validation was performed of both the stemless components and fracture stems.

In one aspect, the invention provides a prosthesis comprising a central body having a longitudinal axis normal to a reference plane that extends through the central body; and a plurality of fins extending laterally from an outer surface of the central body, the plurality of fins being spaced apart around the outer surface of the central body, wherein spacing of the plurality of fins is asymmetric in the reference plane. The prosthesis can be a stemless prosthetic component, e.g., a stemless humeral prosthetic component. In some aspects, a first fin of the plurality of fins has a first fin length, the first fin length defined by a first distance from the central body to an outermost radial edge of the first fin, a second fin of the plurality of fins has a second fin length, the second fin length defined by a second distance from the central body to an outermost radial edge of the second fin. The second fin length can be less than the first fin length. In some aspects, each of the plurality of fins has a proximal fin edge having a proximal edge length and a distal fin edge having a distal edge length.

In some aspects, the proximal edge length of at least one of the plurality of fins is greater than the distal edge length of the at least one of the plurality of fins. In some aspects, the proximal edge length of at least one of the plurality of fins is equal to the distal edge length of the at least one of the plurality of fins. In some aspects, each of the plurality of fins has a lateral fin edge, and at least one of the plurality of fins has a lateral fin edge sloped at an oblique angle with respect to the reference plane.

In some aspects, at least one of the plurality of fins is substantially trapezoidal. In some aspects, at least one of the plurality of fins has rounded fin edges. In some aspects, the central body has a first opening and a second opening, the first opening corresponding to a proximal side of the central body and the second opening corresponding to a distal side of the central body. In some aspects, at least one of the plurality of fins is modular and removeably coupled to the central body. In some aspects, the prosthesis comprises four fins, or five fins, or six fins.

In some aspects, the first opening has a first diameter and the second opening has a second diameter, the first diameter being greater than the second diameter. The central body and the plurality of fins can be dimensioned for implantation into a humerus of a subject. The central body and the plurality of fins can be dimensioned for implantation into a femur of a subject.

In another aspect, the invention provides a prosthesis comprising a central body; and a plurality of fins extending laterally from an outer surface of the central body, the plurality of fins being spaced apart around the outer surface of the central body, wherein at least one of the plurality of fins has an inner perimeter and an outer perimeter, the inner perimeter and the central body defining a window. The prosthesis can be a fracture stem, e.g., a humeral fracture stem. In some aspects, at least one of the fins having the at least one window includes one or more throughholes in a wall defined by the inner perimeter and the outer perimeter of the fin having the at least one window. Each throughhole can be configured to receive a suture. The central body can have a first opening, a second opening, and a hollow region extending between the first opening and the second opening. At least one of the plurality of fins can be modular and removeably coupled to the central body.

In some aspects, the prosthesis can further comprise a bone graft positioned in the at least one window. The prosthesis may further comprise a stem dimensioned to be received by a distal opening in the central body. The prosthesis may further comprise a proximal section having a first articular surface dimensioned to articulate with a second articular surface of a native bone or a prosthetic component, and a stem connected to the central body, the stem being dimensioned to be received by an opening in the central body. In some aspects, the first articular surface can be convex. In other aspects, the first articular surface can be concave. In some aspects, the prosthesis can be a monoblock prosthesis or a modular prosthesis. The central body and the plurality of fins can be dimensioned for implantation into a humerus of a subject.

In some aspects, the prosthesis comprises a first fin and a second fin, the first fin and the second fin being spaced apart around the outer surface of the central body such that the first fin aligns with a greater tuberosity of the humerus and the second fin aligns with a lesser tuberosity of the humerus when the prosthesis is implanted in the humerus. The first fin can have a first perimeter of a first length, and the second fin can have a second perimeter of a second length, and the first length can be greater than the second length. The central body and the plurality of fins can be dimensioned for implantation into a femur of a subject.

In another aspect, the invention provides a prosthesis comprising a central body having a first section and a second section; and a plurality of fins extending laterally from an outer surface of the central body, the plurality of fins being spaced apart around the outer surface of the central body, wherein the first section has a first longitudinal axis and the second section has second longitudinal axis angled with respect to the first longitudinal axis. The prosthesis can be a fracture stem, e.g., a humeral fracture stem. The second section can be removeably coupled to the first section. At least one of the plurality of fins can comprise at least one throughhole. The central body can have a first opening, a second opening, and a hollow region extending between the first opening and the second opening. At least one of the plurality of fins can be modular and removeably coupled to the central body. At least one of the plurality of fins can be configured to align a first fin segment with the first longitudinal axis and align a second fin segment with the second longitudinal axis.

In some aspects, the prosthesis may further comprise a stem dimensioned to be received by a distal opening in the central body. The prosthesis may further comprise a proximal section having a first articular surface dimensioned to articulate with a second articular surface of a native bone or a prosthetic component, and a stem connected to the central body, the stem being dimensioned to be received an opening in the central body. In some aspects, the first articular surface can be convex. In other aspects, the first articular surface can be concave. In some aspects, the prosthesis can be a monoblock prosthesis or a modular prosthesis. The central body and the plurality of fins can be dimensioned for implantation into a humerus of a subject.

In another aspect, the invention provides a kit for implanting a joint component into a bone of a joint wherein the joint component comprises a central body and a plurality of fins extending laterally from an outer surface of the central body. The kit may comprise a trial template having (i) a central ring having a longitudinal axis normal to a reference plane that extends through the central ring, and (ii) a plurality of arms extending laterally from an outer surface of the central ring. The plurality of arms can be spaced apart around the outer surface of the central ring, wherein spacing of the plurality of arms is asymmetric in the reference plane.

In some aspects, the central ring can have a central aperture defined by an inner aperture of the central ring, the central ring can have a wall defined by the inner perimeter and an outer perimeter of the central ring, and the wall includes a passageway for receiving a locator pin. The kit may further comprise a locator tool having a handle connected to the locator pin.

In another aspect, the invention provides a kit for implanting a joint component into a bone of a joint wherein, the joint component comprises a central body and a plurality of fins extending laterally from an outer surface of the central body. The kit can comprise a preparation tool having (i) a central hollow cylinder having a longitudinal axis normal to a reference plane that extends through the central hollow cylinder, and (ii) a plurality of arms extending laterally from an outer surface of the central hollow cylinder. The plurality of arms can be spaced apart around the outer surface of the central hollow cylinder, wherein spacing of the plurality of arms is asymmetric in the reference plane.

In some aspects, spacing of the plurality of arms of the preparation tool corresponds to spacing of the plurality of fins of the joint component, and each of the arms of the preparation tool has a lesser thickness than its corresponding fin of the joint component. The kit may further comprise a cannulated instrument for impacting the preparation tool into the bone.

In another aspect, the invention provides a method for manufacturing a prosthetic component for replacing a part of a bone of a joint in a subject. The method comprises forming the prosthetic component to include a vertical length and a horizontal length. The vertical length and the horizontal length of the prosthetic component can be determined by: (a) creating a three dimensional model from one or more scans of the bone of the joint; (b) positioning on the model a bone cut reference plane that extends to an outer surface of the model; (c) orienting on an image including the bone cut reference plane a first reference line that extends from a first border of a head of the bone to an opposite second border of the head of the bone; (d) orienting on the image a second reference line that extends from a third border of the head of the bone to an opposite fourth border of the head of the bone; (e) determining the vertical length of the prosthetic component from a first length of the first reference line; and (f) determining the horizontal length of the prosthetic component from a second length of the second reference line.

In some aspects, step (a) comprises creating a three dimensional model using multiple scans from a single subject or multiple scans from more than one subject. Manufacturing a prosthetic component may include using additive manufacturing. The prosthetic component can be a stemless prosthetic component or a fracture stem. The image can be processed to remove cortical bone in the bone cut reference plane before orienting the first reference line and the second reference line on the image of the cancellous bone.

In another aspect, the method for manufacturing a prosthetic component may additionally include determining a maximum depth for a prosthetic. The maximum depth of the prosthetic component can be determined by finding an intersection point of the first reference line and the second reference line on the image, or by determining the midpoint of first reference line. After selecting the midpoint or the intersection point, then the depth may be determined by orienting on an image of the model a third reference line that extends from the intersection point to fifth border of the head of the bone and determining the maximum depth of the prosthetic component from the length of the third reference line.

In some aspects, the method may further comprise forming the prosthetic component to include an inclination angle, the inclination angle of the prosthetic component having been determined by (j) orienting on the image of the model an axial reference line; and (k) determining the inclination angle of the prosthetic component from a reference angle between the axial reference line and the bone cut reference plane. In some aspects, step (b) may comprise positioning on the model an anatomic cut reference plane and selecting the anatomic cut reference plane to be the bone cut reference plane. Step (b) may comprise (i) positioning on the model an anatomic cut reference plane, (ii) positioning on the model a second reference plane spaced from the anatomic cut reference plane, and (iii) selecting the second reference plane to be the bone cut reference plane.

In some aspects, the second reference plane can be spaced to be parallel to the anatomic cut reference plane. The second reference plane can be spaced about two to ten millimeters from the anatomic cut reference plane. The second reference plane can be spaced about five millimeters from the anatomic cut reference plane.

In some aspects, the method may further comprise forming the prosthetic component to include a protruding section having a length, the length of the protruding section having been determined by (l) orienting on the image a fourth reference line from the first reference line to a surface of a tuberosity; and (m) determining the length of the protruding section from a fourth length of the fourth reference line. The protruding section can be a fin of a prosthetic component comprising at least one of a stemless prosthetic or a fracture stem.

In some aspects, the method may further comprise forming the prosthetic component to include a protruding section having a length, the length of the protruding section having been determined by (l) orienting on the image a fourth reference line from the midpoint of the first reference line to a surface of a tuberosity; and (m) determining the length of the protruding section from a fourth length of the fourth reference line. The protruding section can be a fin of a prosthetic component consisting of at least one of a stemless prosthetic or a fracture stem.

In some aspects, the method may further comprise forming the prosthetic component to include a protruding section having a length, the length of the protruding section having been determined by (l) determining an intersection point of the first reference line and the second reference line on the image (m) orienting on the image a fourth reference line from the intersection point to a surface of a tuberosity; and (n) determining the length of the protruding section from a fourth length of the fourth reference line. The protruding section can be a fin of a prosthetic component consisting of at least one of a stemless prosthetic or a fracture stem. The prosthetic component can comprise at least one of cobalt chrome, titanium, stainless steel, plastic, and ceramic. The prosthetic component can comprise multiple materials, and one or more additive manufacturing systems may be used to manufacture different parts of the prosthetic component that are assembled for implantation into the patient.

In some aspects, the joint is selected from elbow, wrist, hand, spine, hip, knee, ankle, and foot. When the joint is the elbow, the bone is selected from the ulna, radius and humerus, when the joint is the wrist, the bone is selected from the radius, ulna and carpal bones, when the joint is the hand, the bone is selected from phalanges, metacarpals, and carpals, when the joint is the spine, the bone is a vertebrae, when the joint is the hip, the bone is selected from the femur and the pelvis, when the joint is the knee, the bone is selected from the femur, tibia, and patella, when the joint is the ankle, the bone is selected from the talus, the tibia and the fibula, and when the joint is the foot, the bone is selected from phalanges, tarsals, and metatarsals These and other features, aspects, and advantages of the present invention will become better understood upon consideration of the following detailed description, drawings, and appended claims.

BRIEF DESCRIPTION OF THE DRAWINGS

FIG. 3A is a top view of another prosthetic component of the present disclosure.

FIG. 3B is a side view of the prosthetic component of FIG. 3A.

FIG. 3C is an isometric view of the prosthetic component of FIG. 3A.

FIGS. 4A-4J are top views of various non-limiting embodiments of prosthetic components in accordance with the present disclosure.

FIGS. 5A-5J are side views of the various non-limiting embodiments of FIGS. 4A-4J.

FIG. 7A shows top views of the components of a kit for implanting a joint component into a bone of a joint in accordance with the present disclosure.

FIG. 7B shows top views of one size group of the components of the kit of FIG. 7A.

FIG. 10A is a top view of a proximal component of the fracture stem of FIG. 9A.

FIG. 10B is a side view of the proximal component of FIG. 10A.

FIG. 10C is an isometric view of the proximal component of FIG. 10A.

FIGS. 12A-12J are side views of the various non-limiting embodiments of the proximal component of a fracture stem of FIGS. 11A-11J.

FIG. 23 shows other images of the three dimensional model of a humerus created in accordance with the methodology of this disclosure. Reference lines are placed on the model.

FIG. 27 shows other images of the three dimensional model of a humerus created in accordance with the methodology of this disclosure. Reference planes are placed on the model.

Like reference numerals will be used to refer to like parts from Figure to Figure in the following description of the drawings.

DETAILED DESCRIPTION OF THE INVENTION

Figure 1A:
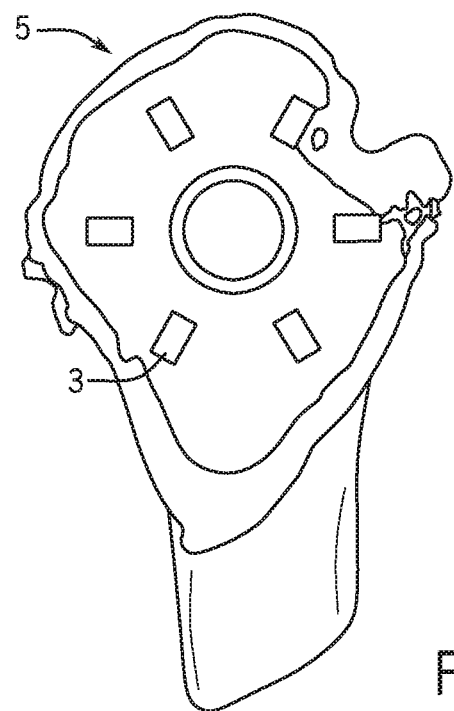
FIG. 1A shows a medial view of a prior art stemless humeral prosthetic component implanted in a resected proximal end of a humerus.
Figure 1B:
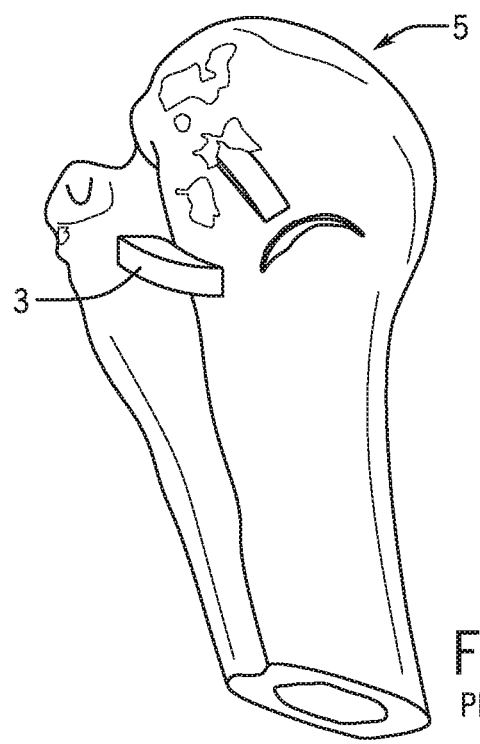
FIG. 1B shows a lateral view of the prior art stemless humeral prosthetic component of FIG. 1A in a resected humerus.

Referring to FIGS. 1A-1B, a prior art prosthetic component 3 is shown positioned within a humerus 5. In this particular instance, the prosthetic component 3 is placed within a deep cut to the humerus 5. Deeper cuts are often necessary, for example with patients that have a rotator cuff insufficiency. As shown by FIG. 1B, even the small prosthetic component 3 is too large for sufficient placement at the specified depth as fins of the prosthetic component 3 pierce the proximal section of the humerus. This can result in the fracturing of the humerus 5, as shown in FIG. 1B. Current prosthetic components are circular in design, however bones are not perfectly circular which can result in complications and failures. Thus, the smallest stemless humeral component placed after a five millimeter deeper cut to accommodate patients with rotator cuff insufficiency would result in fracturing the humerus. As such, an improved prosthetic component is needed.

Figure 2A:
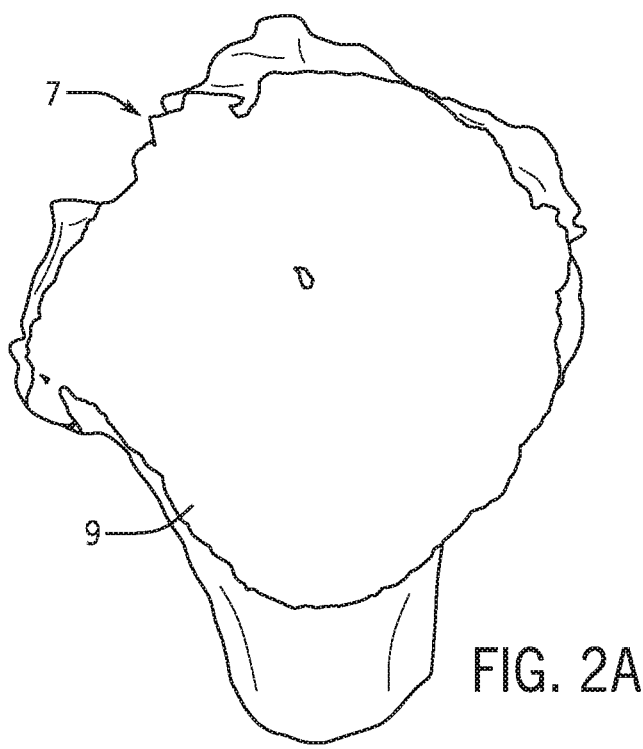
FIG. 2A is cross-sectional view of a resected humerus.
Figure 2B:
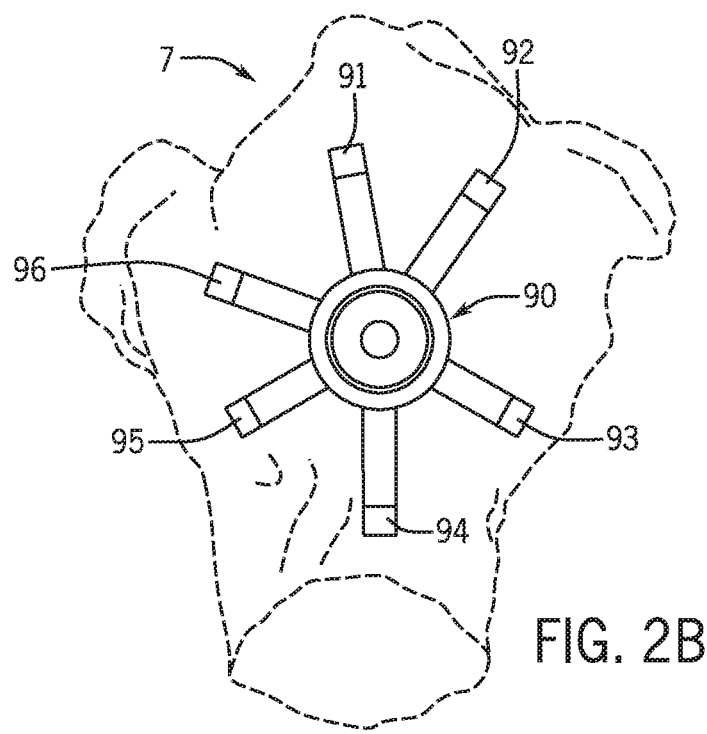
FIG. 2B is a stemless prosthetic component of the present disclosure positioned in a humerus.

Referring to FIGS. 2A and 2B, a humerus 7 may be cut and a surface area 9 of the cut may be determined. A non-limiting example embodiment of a stemless prosthetic component 90 is shown. In comparison to the surface area 9, the stemless prosthetic component 90 may be selected, by a process described below that is able to fit the specific shape and surface area 9 of the patient's humerus 7. FIG. 2B illustrates what the humerus 7 looks like with the stemless prosthetic component 90 positioned within a right shoulder. The stemless prosthetic component 90 has a central ring with fins extending outward from the central ring. A superior fin 91 is placed 10 degrees from the vertical axis. A greater tuberosity fin 92 is placed at 35 degrees from the vertical axis. This is the mean angle among the consecutive series of shoulders studied in the Example below. Three dimensional (3D) modeling revealed that a smaller accessory fin 93 could be added to capture posterior-inferior bone. An inferior fin 94 is used as anatomic modeling revealed a significant amount of bone present inferiorly that could be utilized to improve model fit. In certain sizes, 3D modeling revealed that there was sufficient bone to place a smaller accessory anterior-inferior fin 95. A lesser tuberosity fin 96 is placed at 70 degrees from the vertical axis. This is the mean angle among the consecutive series of shoulders studied in the Example below. It should be noted that for a left shoulder the angle measurements noted here would be mirrored around the vertical axis.

Referring to FIGS. 3A-3C, a non-limiting example embodiment of a stemless prosthetic component 100 is shown. The prosthetic component 100 may be oriented on a longitudinal axis 102 normal to a reference plane 104. The prosthetic component 100 may include a central body 106 wherein the longitudinal axis 102 extends through the central body 106. A plurality of fins may extend from an outer surface 112 on the central body 106. In one non-limiting example, the plurality of fins may be described as including at least a first fin 154 and a second fin 110. The first fin 154 may extend laterally from the central body 106, and may define a first fin length 114. The first fin length 114 may be defined by a first distance from the central body 106 to an outermost radial edge 107a of the first fin 154. Similarly, the second fin 110 may extend laterally from the central body 106, and may define a second fin length 116. The second fin length 116 may be defined by a second distance from the central body 106 to an outermost radial edge 107b of the second fin 110. In some non-limiting embodiments, the second fin length 116 may be less than the first fin length 114.

Still referring to FIGS. 3A-3C, in some embodiments the prosthetic component 100 may include a proximal edge 118 and a distal edge 120. Each of the plurality of fins may have a proximal fin edge having a proximal edge length 122 and a distal fin edge may have a distal edge length 124. In one non-limiting example, the proximal edge length 122 may be greater than the distal edge length 124. In another non-limiting example, the proximal edge length 122 may be equal to the distal edge length 124. The plurality of fins 154, 110 may each include a first lateral fin edge 140a and a second lateral fin edge 140b. In some situations, it may be beneficial to have the first lateral fin edge 140a slope at an oblique angle with respect to the reference plane 104. In some situations, it may be beneficial to have the second lateral fin edge 140b slope at an oblique angle with respect to the reference plane 104. In some situations, it may be beneficial to have the first lateral fin edge 140a perpendicular with respect to the reference plane 104 and the second lateral fin edge 140b slope at an oblique angle with respect to the reference plane 104. In some situations, it may be beneficial to have at least one of the plurality of fins 154, 110 be substantially trapezoidal. In one non-limiting embodiment, at least one of the plurality of fins 154, 110 may have a rounded fin edge 126. In some situations, it may be beneficial for at least one of the plurality of fins 154, 110 to be modular and removeably coupled to the central body 106. Modular fins may allow for a variety of size options. The prosthetic component 100 may be configured and dimensioned for implantation into a humerus of a subject. Alternately, the prosthetic component 100 may be configured and dimensioned for implantation into a femur of a subject. The prosthetic component 100 may include any number of fins, such as four fins, five fins, or six fins. In the prosthetic component 100 of FIGS. 3A-3C, there are four fins 151, 152, 153, 108 in addition to fins 154, 110. The spacing of the fins 108, 110, 151, 152, 153, 154 is asymmetric with respect to the reference plane 104.

Still referring to FIG. 3A-3C, the central body 106 may have a first opening 134 that may have a first diameter 128. Additionally, the prosthetic component 100 may have a second opening 132 that may have a second diameter 130. This second opening 132 may be used as a pass-through for a guidewire. In one non-limiting embodiment, the first diameter 128 may be greater than the second diameter 130. The first opening 134 may correspond to the proximal edge 118. The second opening 132 may correspond to the distal edge 120.

Referring to FIGS. 4A-4J, 5A-5J, and 6A-6J, the prosthetic component 100 is shown as several non-limiting example embodiments. The prosthetic component 100 may have a variety of configurations, and the example embodiments are provided to highlight size differences that may exist between non-limiting embodiments of the prosthetic component 100.

A prosthetic component 100A is one non-limiting example embodiment. FIGS. 4A, 5A, and 6A depict the prosthetic component 100A. A detailed description of the prosthetic component 100A may be in accordance with the previously described prosthetic component 100. The prosthetic component 100A may have five fins. Alternatively, the prosthetic component 100A may have any number of fins. The fins may be asymmetrically spaced around a central body of the prosthetic component 100A. The spacing of the fins around the central body may vary depending upon the desired position of the prosthetic component 100A within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

A prosthetic component 100B is another non-limiting example embodiment. FIGS. 4B, 5B, and 6B depict the prosthetic component 100B. A detailed description of the prosthetic component 100B may be in accordance with the previously described prosthetic component 100. The prosthetic component 100B may have five fins. Alternatively, the prosthetic component 100B may have any number of fins. The fins may be asymmetrically spaced around a central body of the prosthetic component 100B. The spacing of the fins around the central body may vary depending upon the desired position of the prosthetic component 100B within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

A prosthetic component 100C is another non-limiting example embodiment. FIGS. 4C, 5C, and 6C depict the prosthetic component 100C. A detailed description of the prosthetic component 100C may be in accordance with the previously described prosthetic component 100. The prosthetic component 100C may have six fins. Alternatively, the prosthetic component 100C may have any number of fins. The fins may be asymmetrically spaced around a central body of the prosthetic component 100C. The spacing of the fins around the central body may vary depending upon the desired position of the prosthetic component 100C within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

A prosthetic component 100D is another non-limiting example embodiment. FIGS. 4D, 5D, and 6D depict the prosthetic component 100D. A detailed description of the prosthetic component 100D may be in accordance with the previously described prosthetic component 100. The prosthetic component 100D may have six fins. Alternatively, the prosthetic component 100D may have any number of fins. The fins may be asymmetrically spaced around a central body of the prosthetic component 100D. The spacing of the fins around the central body may vary depending upon the desired position of the prosthetic component 100D within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

A prosthetic component 100E is another non-limiting example embodiment. FIGS. 4E, 5E, and 6E depict the prosthetic component 100E. A detailed description of the prosthetic component 100E may be in accordance with the previously described prosthetic component 100. The prosthetic component 100E may have six fins. Alternatively, the prosthetic component 100E may have any number of fins. The fins may be asymmetrically spaced around a central body of the prosthetic component 100E. The spacing of the fins around the central body may vary depending upon the desired position of the prosthetic component 100E within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

A prosthetic component 100F is another non-limiting example embodiment. FIGS. 4F, 5F, and 6F depict the prosthetic component 100F. A detailed description of the prosthetic component 100F may be in accordance with the previously described prosthetic component 100. The prosthetic component 100F may have five fins. Alternatively, the prosthetic component 100F may have any number of fins. The fins may be asymmetrically spaced around a central body of the prosthetic component 100F. The spacing of the fins around the central body may vary depending upon the desired position of the prosthetic component 100F within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

A prosthetic component 100G is another non-limiting example embodiment. FIGS. 4G, 5G, and 6G depict the prosthetic component 100G. A detailed description of the prosthetic component 100G may be in accordance with the previously described prosthetic component 100. The prosthetic component 100G may have five fins. Alternatively, the prosthetic component 100G may have any number of fins. The fins may be asymmetrically spaced around a central body of the prosthetic component 100G. The spacing of the fins around the central body may vary depending upon the desired position of the prosthetic component 100G within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

A prosthetic component 100H is another non-limiting example embodiment. FIGS. 4H, 5H, and 6H depict the prosthetic component 100H. A detailed description of the prosthetic component 100H may be in accordance with the previously described prosthetic component 100. The prosthetic component 100H may have six fins. Alternatively, the prosthetic component 100H may have any number of fins. The fins may be asymmetrically spaced around a central body of the prosthetic component 100H. The spacing of the fins around the central body may vary depending upon the desired position of the prosthetic component 100H within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

A prosthetic component 100I is another non-limiting example embodiment. FIGS. 4I, 5I, and 6I depict the prosthetic component 100I. A detailed description of the prosthetic component 100I may be in accordance with the previously described prosthetic component 100. The prosthetic component 100I may have six fins. Alternatively, the prosthetic component 100I may have any number of fins. The fins may be asymmetrically spaced around a central body of the prosthetic component 100I. The spacing of the fins around the central body may vary depending upon the desired position of the prosthetic component 100I within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

A prosthetic component 100J is another non-limiting example embodiment. FIGS. 4J, 5J, and 6J depict the prosthetic component 100J. A detailed description of the prosthetic component 100J may be in accordance with the previously described prosthetic component 100. The prosthetic component 100J may have six fins. Alternatively, the prosthetic component 100J may have any number of fins. The fins may be asymmetrically spaced around a central body of the prosthetic component 100J. The spacing of the fins around the central body may vary depending upon the desired position of the prosthetic component 100J within a patient. The spacing of the fins around the central body may be changed in advance of a procedure when using fixed position fins. Alternately, the use of modular fins may allow for spacing and sizing flexibility during a procedure. The fins may vary in length and size. The length and size of the central body may vary.

Looking at FIGS. 4A to 4J, FIGS. 5A to 5J, and FIGS. 6A to 6J, it can be seen that prosthetic component 100A is left handed for a left shoulder and corresponds in size to prosthetic component 100F which is right handed for a right shoulder. Likewise, prosthetic component 100B is left handed for a left shoulder and corresponds in size to prosthetic component 100G which is right handed for a right shoulder; prosthetic component 100C is left handed for a left shoulder and corresponds in size to prosthetic component 100H which is right handed for a right shoulder; prosthetic component 100D is left handed for a left shoulder and corresponds in size to prosthetic component 100I which is right handed for a right shoulder; and prosthetic component 100E is left handed for a left shoulder and corresponds in size to prosthetic component 100J which is right handed for a right shoulder.

Figure 5K:
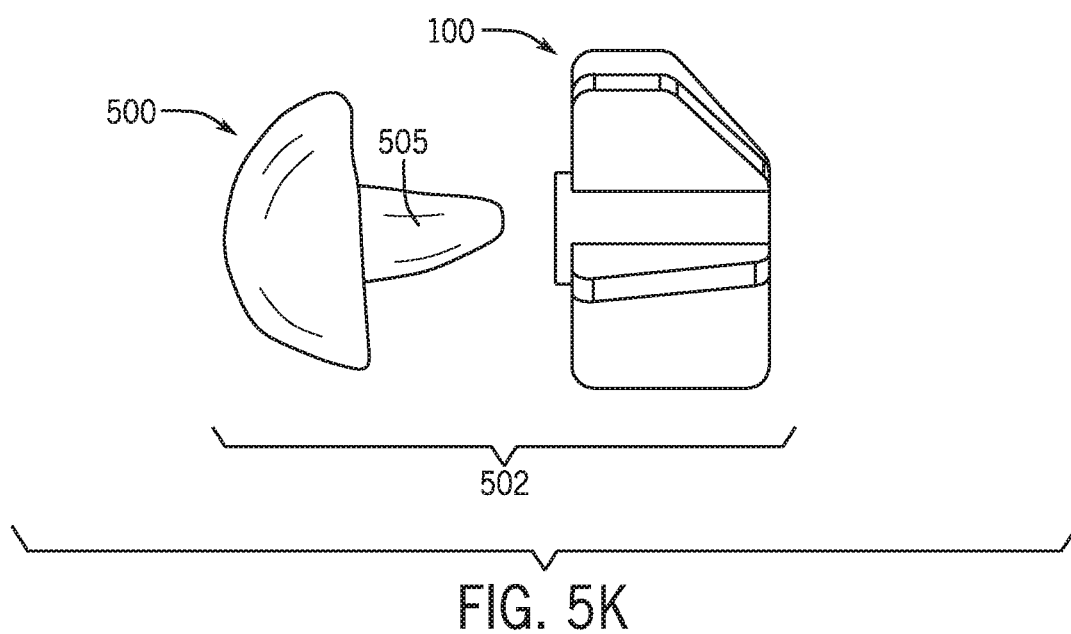
FIG. 5K is an exploded side view of a prosthetic device in accordance with the present disclosure.
Figure 6E:
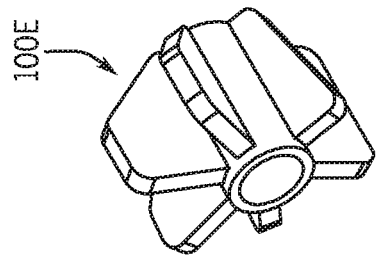
FIGS. 6A-6J are isometric views of the various non-limiting embodiments of FIGS. 4A-4J.
Figure 6J:
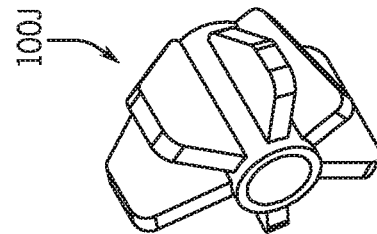
Figure 6D:
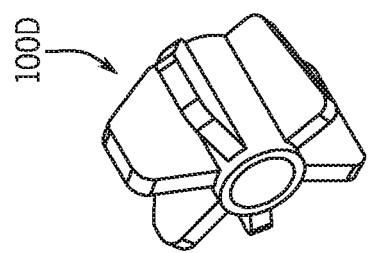
Figure 6I:
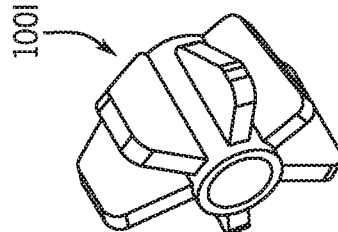
Figure 6C:
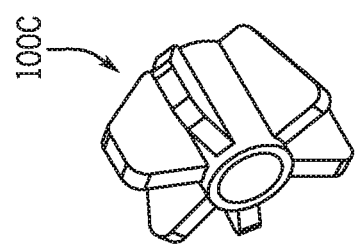
Figure 6H:
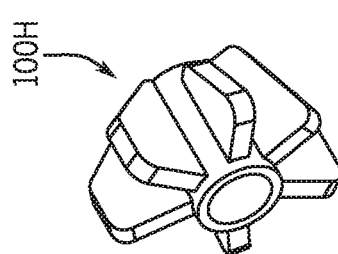
Figure 6B:
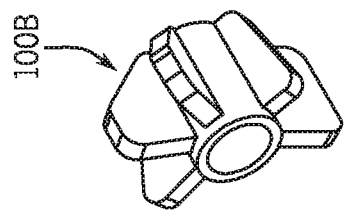
Figure 6G:
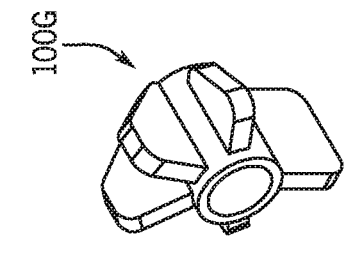
Figure 6A:
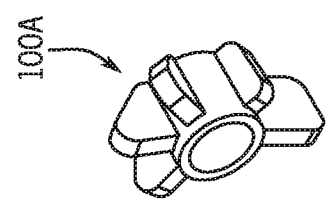
Figure 6F:
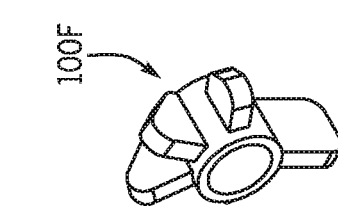

Referring to FIG. 5K, two non-limiting example embodiments of a prosthetic device are shown. A prosthetic device 502 may include the stemless prosthetic component 100 and a proximal section 500. The proximal section 500 may include a first articular surface dimensioned to articulate with a second articular surface of a native bone or a second prosthetic component. The first articular surface may be convex. A non-limiting example embodiment of a convex proximal section 500 is shown by FIG. 5K. The prosthetic component 100 may be configured to receive a trunnion 505 of the proximal section 500.

Figure 5L:
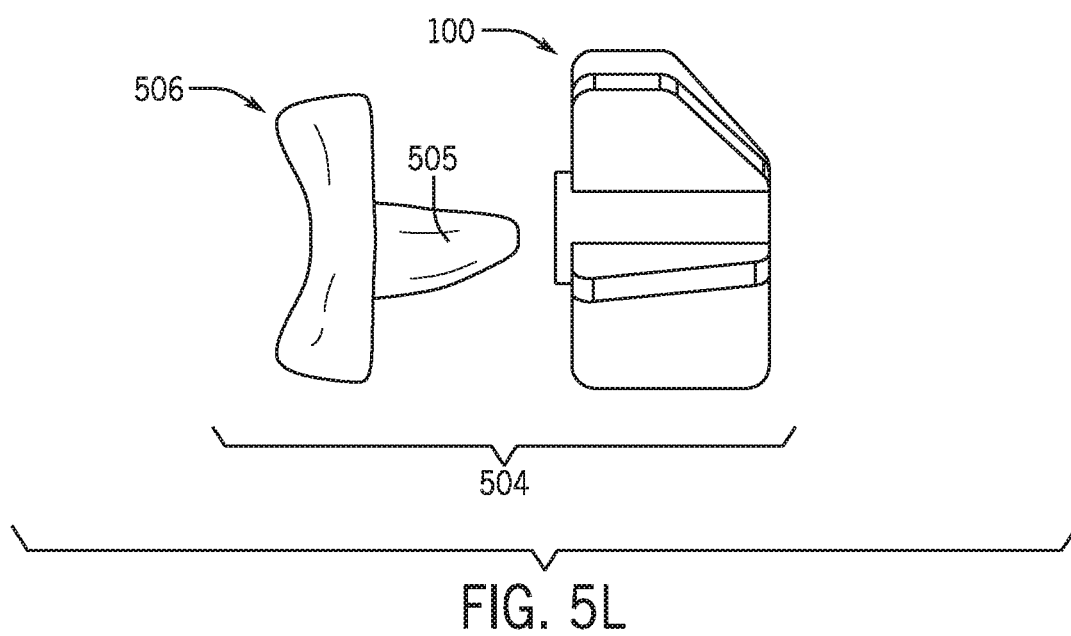
FIG. 5L is an exploded side view of another prosthetic device in accordance with the present disclosure.

Referring to FIG. 5L, a prosthetic device 504 may include the stemless prosthetic component 100 and a proximal section 506. The proximal section 506 may include a first articular surface dimensioned to articulate with a second articular surface of a second prosthetic component. The first articular surface may be concave. A non-limiting example embodiment of a concave proximal section 506 is shown by FIG. 5L. The prosthetic component 100 may be configured to receive a trunnion 505 of the proximal section 506.

Referring to FIGS. 7A-7B, a non-limiting example kit 700 for implanting a prosthetic component selected from prosthetic components 100 to 100J into the bone of a joint is shown. The kit 700 may include a trial template 714, which may be selected from a plurality of trial templates, as shown by row 702. The kit 700 may also include a preparation tool 716, which may be selected from a plurality of preparation tools, as shown by row 704. The kit 700 may also include a stemless prosthetic component 100, which may be selected from a plurality of prosthetic components, as shown by row 718. The selection of the trial template 714, the preparation tool 716, and the prosthetic component 100 may be made based upon certain bone attributes including, but not limited to, surface area, depth, volume and/or cross-sectional shape. The kit 700 may include a cannulated instrument 706. The kit 700 may include a locator tool 708. The locator tool 708 may include a handle 710 attached to a locator pin 712. The locator tool 708 may be used in a placement of the trial template 714. The preparation tool 716 may have a plurality of arms 715 extending from a central ring. The arms 715 of preparation tool 716 may be proportionally smaller when compared to the fins of the prosthetic component 100. This size difference may help the fins of the prosthetic component 100 achieve a tight fit when placed within the bone. The trial template 714 may have a plurality of arms extending from a central ring. The arms of trial template 714 may correlate to the location of the fins of a prosthetic component 100 to help a physician visualize how a prosthetic component 100 may fit in a patient's anatomy when beginning a procedure. The preparation tool 716 and the trial template 714 may be used to help guide the placement of the prosthetic component 100.

The following non-limiting example describes one way in which the kit 700 may be used for implanting a prosthetic component 100 into the bone of a joint. The bone head may be cut along a plane. The trial template 714 may be positioned along the plane. The locator tool 708 may be used to position the trial template 714 on the resected bone. Specifically, the locator pin 712 may or may not extend into the bone via a through-hole on the trial template 714. A guidewire may then be placed into the bone, which may help with the positioning of the preparation tool 716 and/or the prosthetic component 100. The trial template 714 may be removed after the placement of the guidewire. A drill may be introduced over the guidewire to create a central channel. The preparation tool 716 may be positioned on the bone and may use the guidewire to guide its placement. The preparation tool 716 may be pressed into the bone. The preparation tool 716 may then be removed from the bone after having made a guiding path for the prosthetic component 100. The prosthetic component 100 may be positioned to align with the recesses left in the bone by the arms 715 of the preparation tool 716. The cannulated instrument 706 may be used to impact the prosthetic component 100 into the bone. The cannulated instrument 706 may help the prosthetic component 100 achieve a tight fit within the bone. The proximal fin edges may lie flush with the cut plane of the bone. The guidewire may be removed from the bone, and additional tools may be used to alter or reposition the prosthetic component 100 within the bone. Once the prosthetic component 100 is positioned within the bone, a proximal section (such as 500 or 506 of FIGS. 5K-5L) may be placed in an opening of the central body.

Figure 8:
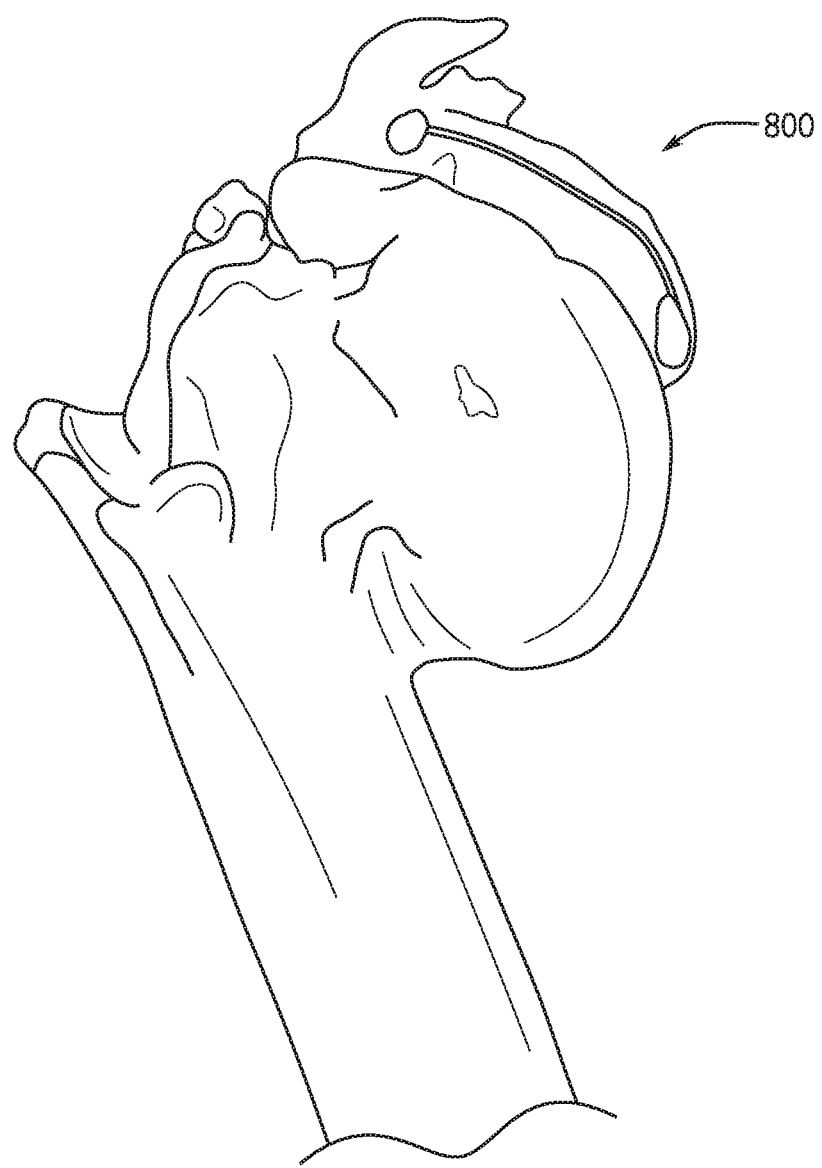
FIG. 8 shows a humerus with fractured proximal section.

Referring now to FIG. 8, a fractured proximal section of a humerus 800 is shown. Surgically repairing the fractured humerus 800 may be simplified as described herein.

Figure 9C:
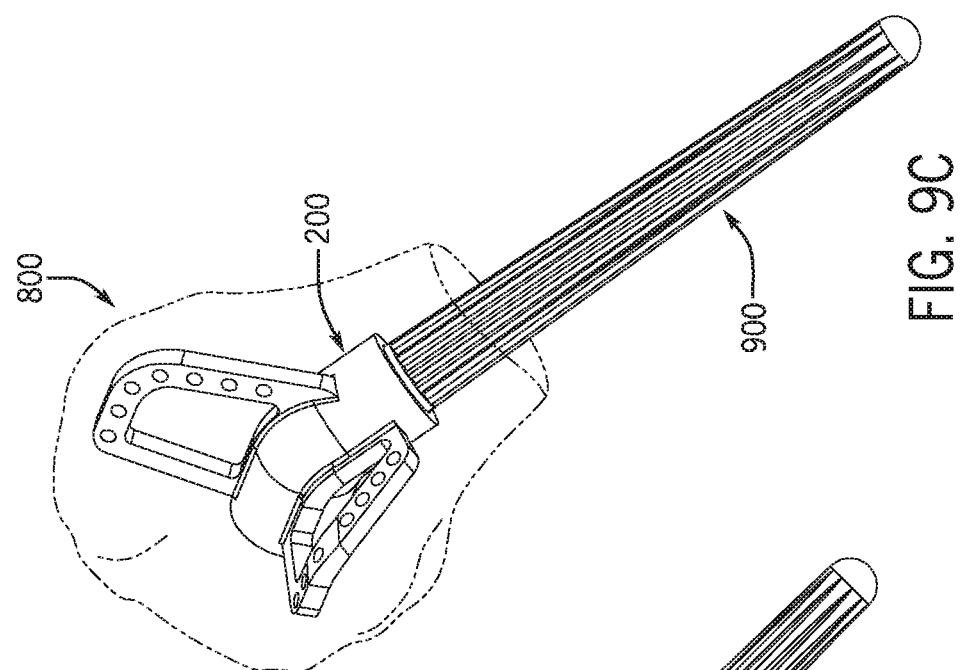
FIG. 9C is another perspective view of the fracture stem of FIG. 9A implanted in a humerus.
Figure 9B:
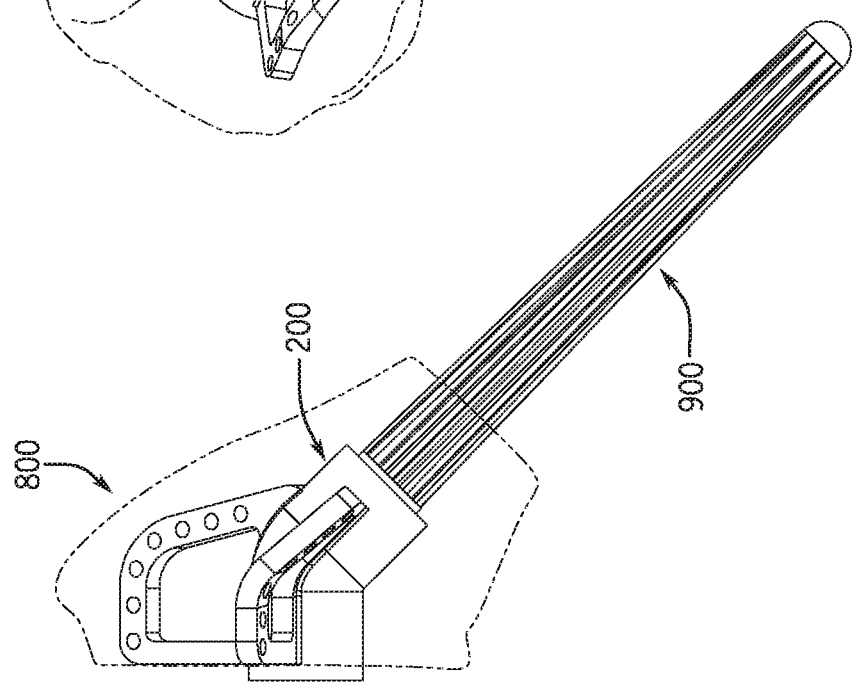
FIG. 9B is a side view of the fracture stem of FIG. 9A implanted in a humerus.
Figure 9A:
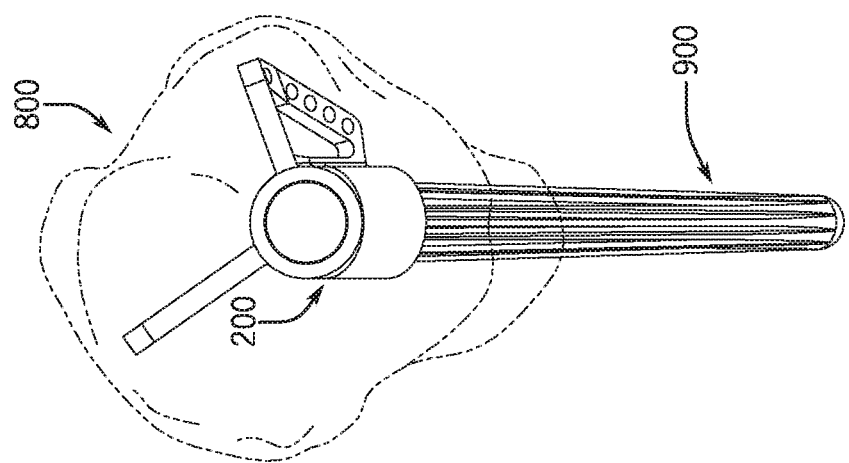
FIG. 9A is a top perspective view of a fracture stem in accordance with the present disclosure implanted in a humerus.

Referring to FIGS. 9A-9C, one non-limiting example embodiment of a prosthetic device 200 is shown. The prosthetic device 200 may be implanted into the fractured bone 800. The prosthetic device 200 may include a stem 900. The stem 900 may be positioned within a portion of the fractured bone 800.

Referring to FIGS. 10A-10C, the prosthetic device 200 is shown. The prosthetic component 200 may be oriented on a first longitudinal axis 202 normal to a reference plane 204. The prosthetic component 200 may include a central body 228. The central body 228 may include a first section 252 that is substantially parallel to the first longitudinal axis 202. The central body 228 may include a second section 250 that is substantially parallel to a second longitudinal axis 206. The second longitudinal axis 206 may be at an angle with respect to the first longitudinal axis 202. The first section 252 may be removeably coupled to the second section 250. A plurality of fins may extend from an outer surface 212 on the central body 228. In one-non-limiting example, the plurality of fins may be described as including a first fin 208 and a second fin 210. The first fin 208 may extend laterally from the central body 228, and may define a first fin length 214. The first fin length 214 may be defined by a first distance from the central body 228 to an outermost radial edge 207a of the first fin 208. Similarly, the second fin 210 may extend laterally from the central body 228, and may define a second fin length 216. The second fin length 216 may be defined by a second distance from the central body 228 to an outermost radial edge 207*b* of the second fin 210. In some non-limiting embodiments, the second fin length 216 may be less than the first fin length 214.

Still referring to FIGS. 10A-10C, in some embodiments one of the plurality of fins may include an outer perimeter 244 and an inner perimeter 242. The area between the outer perimeter 244 and the inner perimeter 242 may be defined by a wall 246. The space defined by the inner perimeter 242 and the central body 228 may be a window 234. The wall 246 may include a through-hole or a plurality of through-holes 236, and the through-hole 236 may be configured to receive a stitch or a suture. A plurality of through-holes 236 may be configured to receive stitches to help hold portions of the fractured bone 800 together.

Still referring to FIGS. 10A-10C, in some embodiments the prosthetic component 100 may include a proximal edge 218 and a distal edge 220. Each of the plurality of fins may have a proximal fin edge having a proximal edge length 222 and a distal fin edge may have a distal edge length 248. In one non-limiting example, the proximal edge length 222 may be greater than the distal edge length 248. In another non-limiting example, the proximal edge length 222 may be equal to the distal edge length 248. The plurality of fins may each include a first lateral fin edge 240*a* and a second lateral fin edge 240*b*. In some situations, it may be beneficial to have the first lateral fin edge 240*a* slope at an oblique angle with respect to the reference plane 204. In some situations, it may be beneficial to have the second lateral fin edge 240*b* slope at an oblique angle with respect to the reference plane 204. In some situations, it may be beneficial to have the first lateral fin edge 240*a* perpendicular with respect to the reference plane 204 and the second lateral fin edge 240*b* slope at an oblique angle with respect to the reference plane 204. In some situations, it may be beneficial to slope the second lateral fin edge 240*b* so that the second lateral fin edge 240*b* is parallel to the second longitudinal axis 206. In some situations, it may be beneficial to have at least one of the plurality of fins be substantially trapezoidal. In one non-limiting embodiment, at least one of the plurality of fins may have a rounded fin edge 226. In some situations, it may be beneficial for at least one of the plurality of fins to be modular and removeably coupled to the central body 228. Modular fins may allow for a variety of size options. The prosthetic component 200 may be configured and dimensioned for implantation into a humerus of a subject. Alternately, the prosthetic component 200 may be configured and dimensioned for implantation into a femur of a subject. The prosthetic component 200 may include any number of fins, such as two fins, three fins, four fins, five fins, or six fins. The spacing of the fins is asymmetric with respect to the reference plane 204. In some situations, it may be beneficial to use the window 234 in any or all of the fins, as defined by the inner perimeter 242 and the central body 228, to position bone graft.

Still referring to FIG. 10A-10C, the central body 228 may have a first opening 224 that may have a first diameter 230. Additionally, the prosthetic component 200 may have a second opening 232 that may have a second diameter (not shown). In one non-limiting embodiment, the first diameter 230 may be greater than the second diameter. The first opening 224 may correspond to the proximal edge 218. The first opening 224 may depict the opening of a friction fit connection, such as a taper lock, where the friction fit connection is configured to receive a connection to a humeral prosthesis, such as a head or a humeral tray. The second opening 232 may correspond to the distal edge 220. The second opening 232 may depict the opening of a friction fit connection, such as a taper lock, where the friction fit connection is configured to receive a connection to a stem. A hollow region 238 may extend from the first opening 224 to the second opening 232. Alternatively, the hollow region 238 may be separated by material that separates the hollow region into two distinct friction fit connections, such as taper locks, associated with the first opening 224 and the second opening 232 respectively.

Referring to FIGS. 11A-11J, 12A-12J, and 13A-13J, the prosthetic component 200 is shown as several different non-limiting example embodiments. The prosthetic component 200 may have a variety of configurations, and the example embodiments are provided to highlight size differences that may exist between non-limiting embodiments of the prosthetic component 200.

Figure 11E:
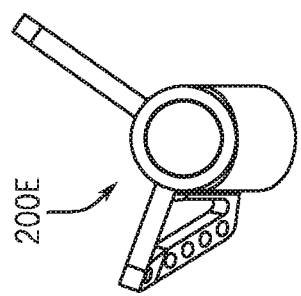
FIGS. 11A-11J are top views of various non-limiting embodiments of the proximal component of a fracture stem in accordance with the present disclosure.
Figure 11D:
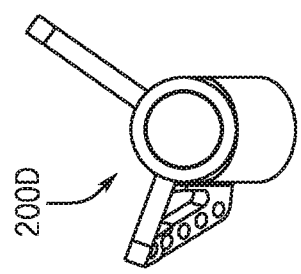
Figure 11C:
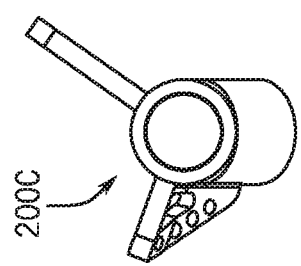
Figure 11B:
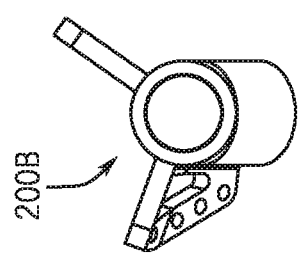
Figure 11A:
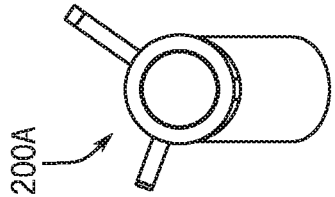
Figure 13E:
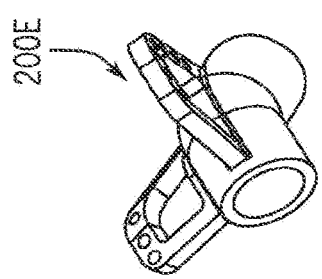
FIGS. 13A-13J are isometric views of the various non-limiting embodiments of the proximal component of a fracture stem of FIGS. 11A-11J.
Figure 13D:
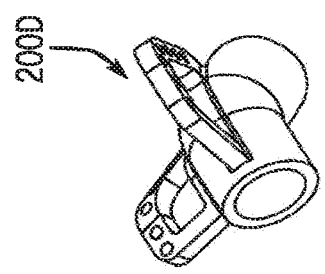
Figure 13C:
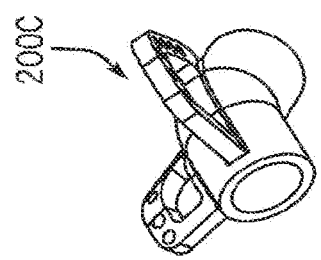
Figure 13B:
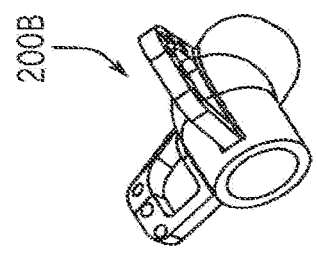
Figure 13A:
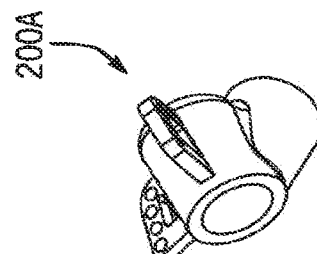

A prosthetic component 200A is one non-limiting example embodiment. FIGS. 11A, 12A, and 13A depict the prosthetic component 200A. A detailed description of the prosthetic component 200A may be in accordance with the previously described prosthetic component 200. The prosthetic component 200A may have two fins. Alternatively, the prosthetic component 200A may have any number of fins. The fins may be asymmetrically spaced around a central body of the prosthetic component 200A. The spacing of the fins around the central body may vary depending upon the desired position of the prosthetic component 200A within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

A prosthetic component 200B is another non-limiting example embodiment. FIGS. 11B, 12B, and 13B depict the prosthetic component 200B. A detailed description of the prosthetic component 200B may be in accordance with the previously described prosthetic component 200. The prosthetic component 200B may have two fins. Alternatively, the prosthetic component 200B may have any number of fins. The fins may be asymmetrically spaced around a central body of the prosthetic component 200B. The spacing of the fins around the central body may vary depending upon the desired position of the prosthetic component 200B within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

A prosthetic component 200C is another non-limiting example embodiment. FIGS. 11C, 12C, and 13C depict the prosthetic component 200C. A detailed description of the prosthetic component 200C may be in accordance with the previously described prosthetic component 200. The prosthetic component 200C may have two fins. Alternatively, the prosthetic component 200C may have any number of fins. The fins may be asymmetrically spaced around a central body of the prosthetic component 200C. The spacing of the fins around the central body may vary depending upon the desired position of the prosthetic component 200C within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

A prosthetic component 200D is another non-limiting example embodiment. FIGS. 11D, 12D, and 13D depict the prosthetic component 200D. A detailed description of the prosthetic component 200D may be in accordance with the previously described prosthetic component 200. The prosthetic component 200D may have two fins. Alternatively, the prosthetic component 200D may have any number of fins. The fins may be asymmetrically spaced around a central body of the prosthetic component 200D. The spacing of the fins around the central body may vary depending upon the desired position of the prosthetic component 200D within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

A prosthetic component 200E is another non-limiting example embodiment. FIGS. 11E, 12E, and 13E depict the prosthetic component 200E. A detailed description of the prosthetic component 200E may be in accordance with the previously described prosthetic component 200. The prosthetic component 200E may have two fins. Alternatively, the prosthetic component 200E may have any number of fins. The fins may be asymmetrically spaced around a central body of the prosthetic component 200E. The spacing of the fins around the central body may vary depending upon the desired position of the prosthetic component 200E within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

Figure 11J:
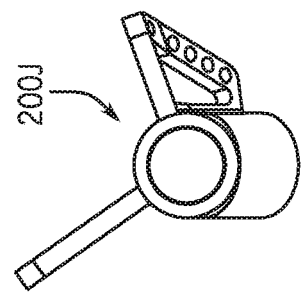
Figure 11I:
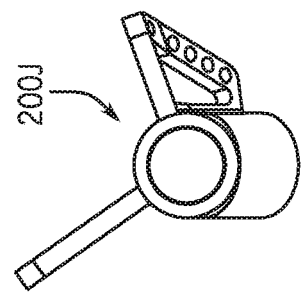
Figure 11H:
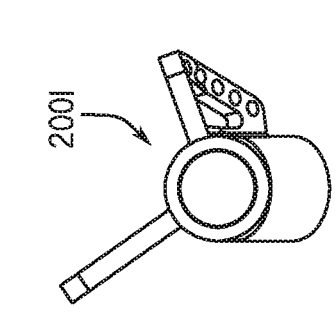
Figure 11G:
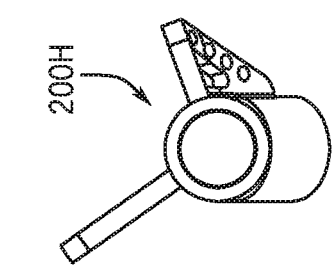
Figure 11F:
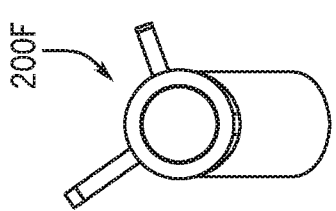
Figure 13J:
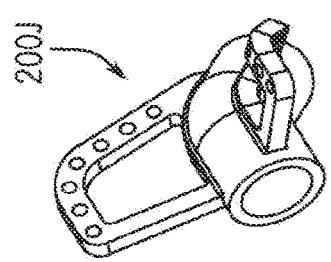
Figure 13I:
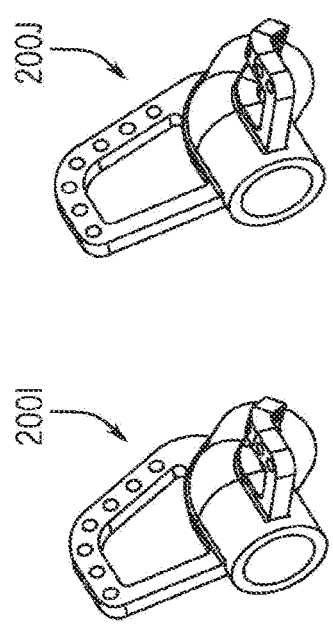
Figure 13H:
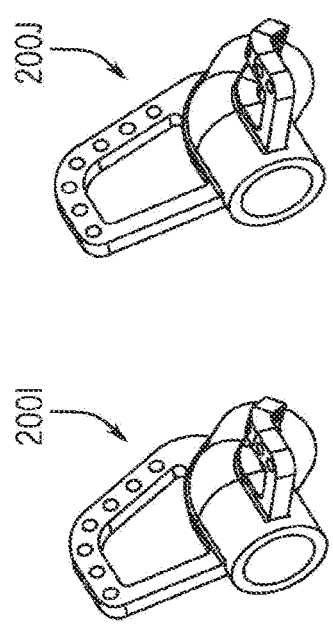
Figure 13G:
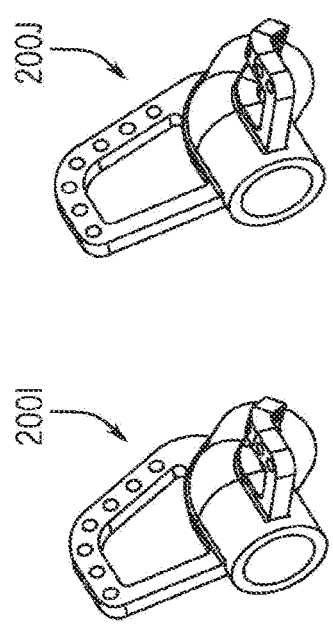
Figure 13F:
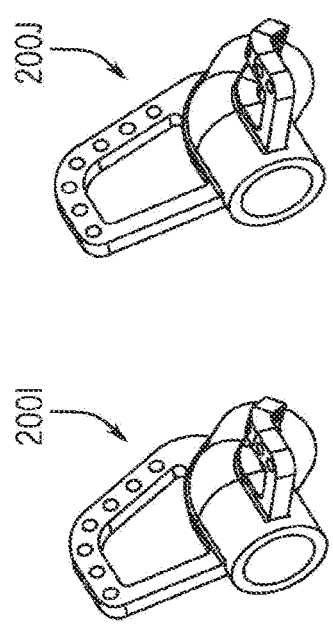

A prosthetic component 200F is another non-limiting example embodiment. FIGS. 11F, 12F, and 13F depict the prosthetic component 200F. A detailed description of the prosthetic component 200F may be in accordance with the previously described prosthetic component 200. The prosthetic component 200F may have two fins. Alternatively, the prosthetic component 200F may have any number of fins. The fins may be asymmetrically spaced around a central body of the prosthetic component 200F. The spacing of the fins around the central body may vary depending upon the desired position of the prosthetic component 200F within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

A prosthetic component 200G is another non-limiting example embodiment. FIGS. 11G, 12G, and 13G depict the prosthetic component 200O. A detailed description of the prosthetic component 200G may be in accordance with the previously described prosthetic component 200. The prosthetic component 200G may have two fins. Alternatively, the prosthetic component 200G may have any number of fins. The fins may be asymmetrically spaced around a central body of the prosthetic component 200G. The spacing of the fins around the central body may vary depending upon the desired position of the prosthetic component 200G within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

A prosthetic component 200H is another non-limiting example embodiment. FIGS. 11H, 12H, and 13H depict the prosthetic component 200H. A detailed description of the prosthetic component 200H may be in accordance with the previously described prosthetic component 200. The prosthetic component 200H may have two fins. Alternatively, the prosthetic component 200H may have any number of fins. The fins may be asymmetrically spaced around a central body of the prosthetic component 200H. The spacing of the fins around the central body may vary depending upon the desired position of the prosthetic component 200H within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

A prosthetic component 200I is another non-limiting example embodiment. FIGS. 11I, 12I, and 13I depict the prosthetic component 200I. A detailed description of the prosthetic component 200I may be in accordance with the previously described prosthetic component 200. The prosthetic component 200I may have two fins. Alternatively, the prosthetic component 200I may have any number of fins. The fins may be asymmetrically spaced around a central body of the prosthetic component 200I. The spacing of the fins around the central body may vary depending upon the desired position of the prosthetic component 200I within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

A prosthetic component 200J is another non-limiting example embodiment. FIGS. 11J, 12J, and 13J depict the prosthetic component 200J. A detailed description of the prosthetic component 200J may be in accordance with the previously described prosthetic component 200. The prosthetic component 200J may have two fins. Alternatively, the prosthetic component 200J may have any number of fins. The fins may be asymmetrically spaced around a central body of the prosthetic component 200J. The spacing of the fins around the central body may vary depending upon the desired position of the prosthetic component 200J within a patient. The spacing of the fins around the central body may be changed in advance of a procedure when using fixed position fins. Alternately, the use of modular fins may allow for spacing and sizing flexibility during a procedure. When the fins are fixed to the central body, adjustment of positioning in the patient may be achieved by rotating the body with respect to the stem to the desired position. The fins may vary in length and size. The length and size of the central body may vary.

Looking at FIGS. 11A to 11J, FIGS. 12A to 12J, and FIGS. 13A to 13J, it can be seen that prosthetic component 200A is right handed for a right shoulder and corresponds in size to prosthetic component 200F which is left handed for a left shoulder. Likewise, prosthetic component 200B is right handed for a right shoulder and corresponds in size to prosthetic component 200G which is left handed for a left shoulder; prosthetic component 200C is right handed for a right shoulder and corresponds in size to prosthetic component 200H which is left handed for a left shoulder; prosthetic component 200D is right handed for a right shoulder and corresponds in size to prosthetic component 200I which is left handed for a left shoulder; and prosthetic component 200E is right handed for a right shoulder and corresponds in size to prosthetic component 200J which is left handed for a left shoulder.

Figure 14:
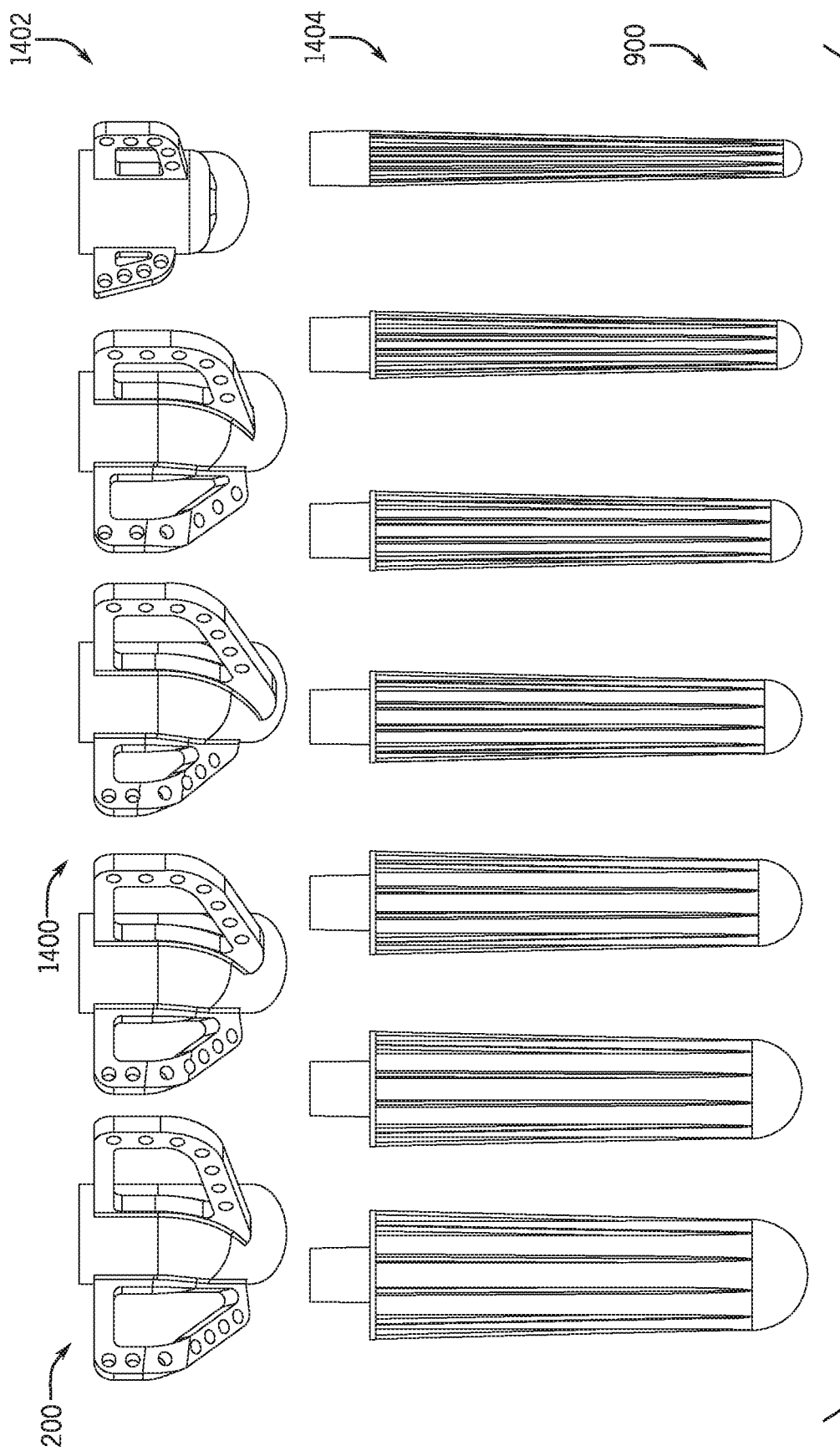
FIG. 14 is a top view of a fracture stem kit in accordance with the present disclosure.

Referring to FIG. 14, a non-limiting example kit 1400 is shown for implanting a prosthetic component selected from prosthetic components 200A to 200J into the bone of a joint. The kit 1400 may include a plurality of prosthetic components 200A to 200J. The prosthetic components 200A to 200J may have varying sizes and dimensions. Row 1402 shows several non-limiting example prosthetic components 200. The kit 1400 may include a plurality of stems 900. The stems 900 may have varying sizes and dimensions. Row 1404 shows several non-limiting example stems 900. One stem 900 and one prosthetic component 200 may be selected from rows 1402, 1404 for a given bone. The selection may be based on a number of bone qualities including, but not limited to, cross-sectional surface area, length, proximal humeral anatomy size, shape, depth and dimensions, and/or fracture history.

Example

The following Example has been presented in order to further illustrate the invention and is not intended to limit the invention in any way.

A. Background

There has been a drive towards bone preserving and less invasive procedures. However, significant deficiencies have been found in currently available devices, specifically they are not anatomic in shape. Many of the devices used are round with a uniform shape. As devices become smaller to accommodate less invasive procedures and are placed under increased stress at the device bone interface, there has been concern about early catastrophic loosening as well as long term bone ingrowth. In an effort for surgeons to maximize contact with native bone, there is a growing tendency for intra-operative fractures due to surgeons forcing a non-anatomic device in an anatomic space or placing an implant that penetrates the cortical bone creating a substantial risk of a stress riser with increased risk of future fracture.

In order to have an implant that maximizes contact with the best quality humeral bone, one needs an implant that matches the proximal humeral anatomy. This disclosure also characterizes that the proximal humeral anatomy is not uniform. Therefore, if humeral cuts are made at different levels of the proximal humerus, the underlying architecture and three dimensional structure is different. This difference has not been previously taken into consideration with humeral devices. In addition, the distribution of implant sizes available should be based on a true anatomic distribution as well as side specific implants. The current method maximizes device contact with native bone and minimizes risk of fracture.

There has been increasing use of shoulder devices for proximal humeral fracture worldwide. This has been associated with a high rate of tuberosity resorption and non-healing leading to sub-optimal results. Current device designs and sizes available are not based on an anatomic distribution and are not anatomic in shape. This method facilitates designing a fracture stem or fixation device with a proximal humeral body that is anatomic. In addition, the methodology facilitates designing the shape and size of fins for tuberosity fixation that are based on the true anatomy of patients undergoing these procedures. Currently, fins for tuberosity attachment are not anatomic in size, shape, and relative angular position to humeral stem.

In addition, humeral components used for shoulder arthroplasty in the setting of a fracture have been traditionally cemented to maintain control of rotation and height. Advantages of uncemented stems for the treatment of humerus fractures would include shorter operating room time, avoidance of morbidity associated with the use of cement, and the ability to change intra-operatively the alignment of the humeral prosthesis. However, recent research indicates a high level of stress shielding, tuberosity resorption, and unsatisfactory outcomes with current uncemented humeral stems with reverse arthroplasty for fracture. Using a rectangular proximal stem geometry designed for the proximal metaphysis and placing it more distally into the diaphysis to get press fit has a high rate of stress shielding and bone resorption. In addition, placing the stem too far distal to obtain an interference fit increases the stress on the tuberosity repair. These disappointing outcomes resulted in the comprehensive investigation of this Example into the cause of this problem and the resultant novel methodology to address this significant problem.

B. Project Resources

A unique database of fifty consecutive high resolution thin cut two dimensional and three dimensional CT scans with a custom designed bone stock protocol of patients who have undergone anatomic shoulder arthroplasty by one of the inventors was available for study. This custom designed protocol was specifically developed for a detailed understanding of the anatomy of patients with shoulder arthritis. In addition, three dimensional (3D) modeling of each of these patients was performed. A novel method for understanding proximal humeral anatomy was subsequently developed using this unique resource and underwent biomechanical testing and cadaveric validation.

In addition, a separate study was undertaken that included one hundred thirty consecutive patients who underwent shoulder arthroplasty for fracture. This study revealed key features that would assist the surgeon at the time of arthroplasty to anatomically place the humeral component and repair the tuberosities with an implant designed to facilitate bone healing.

C. Method and Implications

1. Proximal Humeral Anatomy

Using the above database of two dimensional and three dimensional CT scans of the shoulder joint, three dimensional models of the humerus were created. Looking at FIG. 15, an anatomic humeral head cut reference plane HHC was placed on an image of a three dimensional model H of a humerus from the database. The cortical bone was subtracted and all subsequent measurements were based on the inner cancellous bone. The cancellous bone is the portion of the bone where the humeral prosthetic component is placed. Therefore, the methodology of this Example facilitated an understanding the true anatomy where humeral prosthetic components are placed and helps avoids fracturing the outer cortical bone when a humeral prosthetic component is placed.

2. Anatomic Humeral Head Cut

Figure 16:
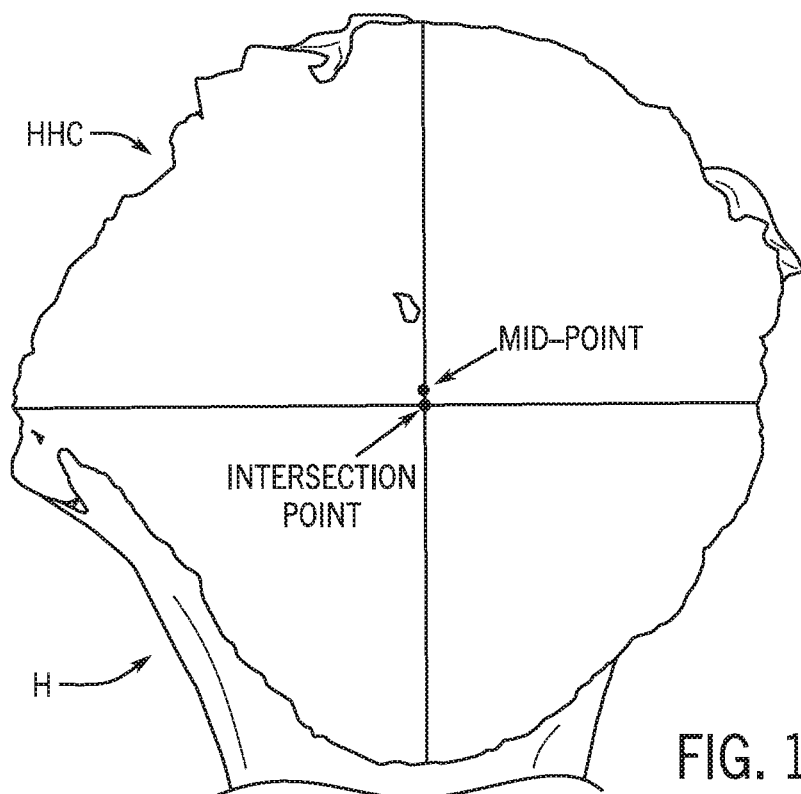
FIG. 16 is another image of the three dimensional model of a humerus created in accordance with the methodology of this disclosure. Reference lines and points are placed on the model.

In FIG. 16, reference lines and reference points were placed on the three dimensional model H. The vertical reference line is the greatest vertical distance on the cut face of the humerus from the lowest point to highest point measured in millimeters; the horizontal reference line is the widest horizontal distance on the cut face of the humerus measured in millimeters; the mid-point is the point that is half of the vertical line; and the intersection point is where the vertical and horizontal lines intersect.

Figure 17:
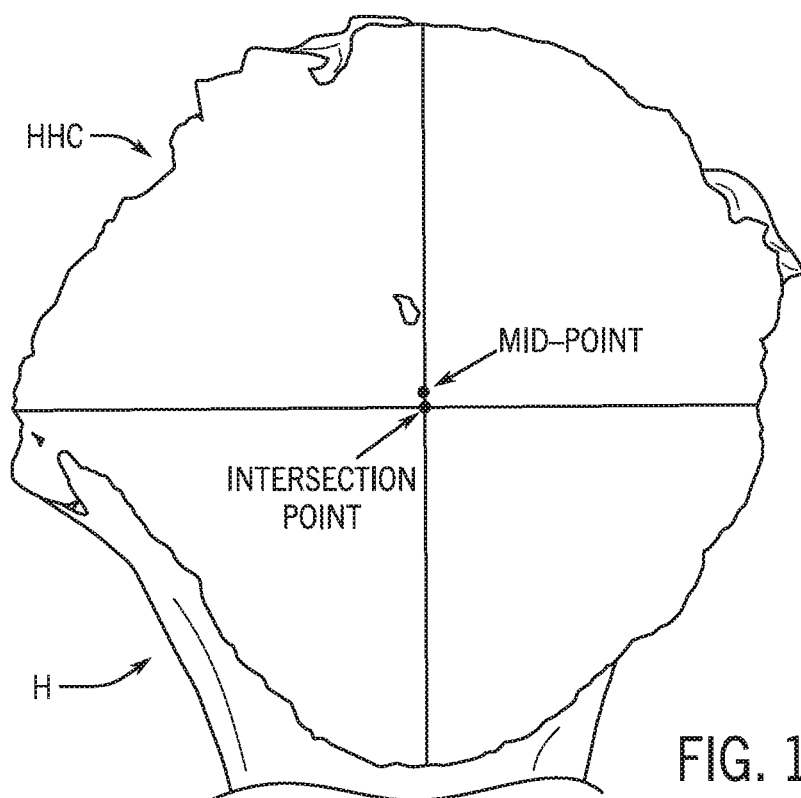
FIG. 17 is another image of the three dimensional model of a humerus created in accordance with the methodology of this disclosure. Reference lines and points are placed on the model.

In FIG. 17, reference lines and reference points were placed on the three dimensional model H. Delta is the distance measured from the mid-point to the intersection point in millimeters. Delta is positive when the intersection point is above the mid-point and negative when the intersection point is below the mid-point. In a perfect circle, these would overlap.

Figure 18:
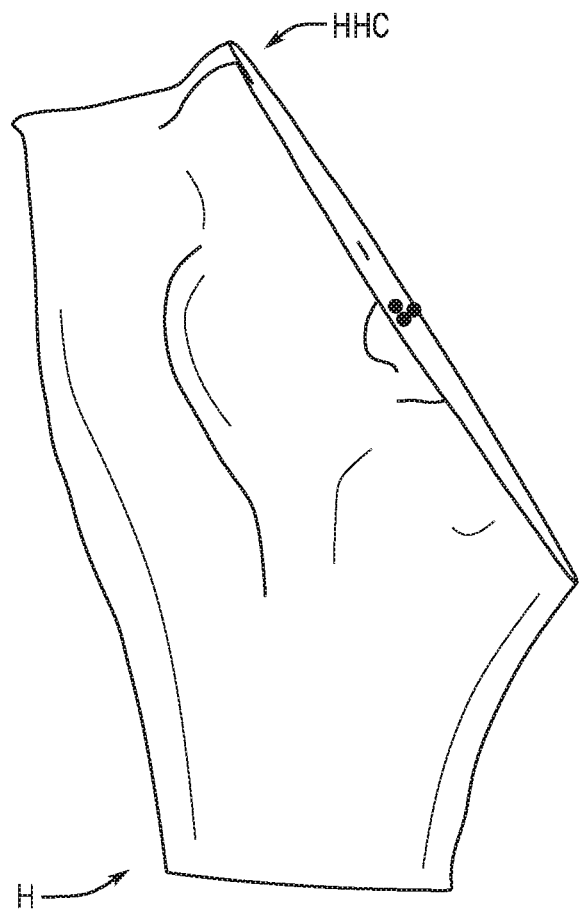
FIG. 18 is another image of the three dimensional model of a humerus created in accordance with the methodology of this disclosure. Reference lines and points are placed on the model.

In FIG. 18, reference lines and reference points were placed on the three dimensional model H. The depth from the mid-point is the depth from mid-point to lateral edge of humerus. The maximum depth of a humeral prosthetic component may be from this point. In FIG. 18, the depth from intersection point is the depth from intersection point to lateral edge of humerus. The maximum depth of a humeral prosthetic component may be from this point.

Figure 19:
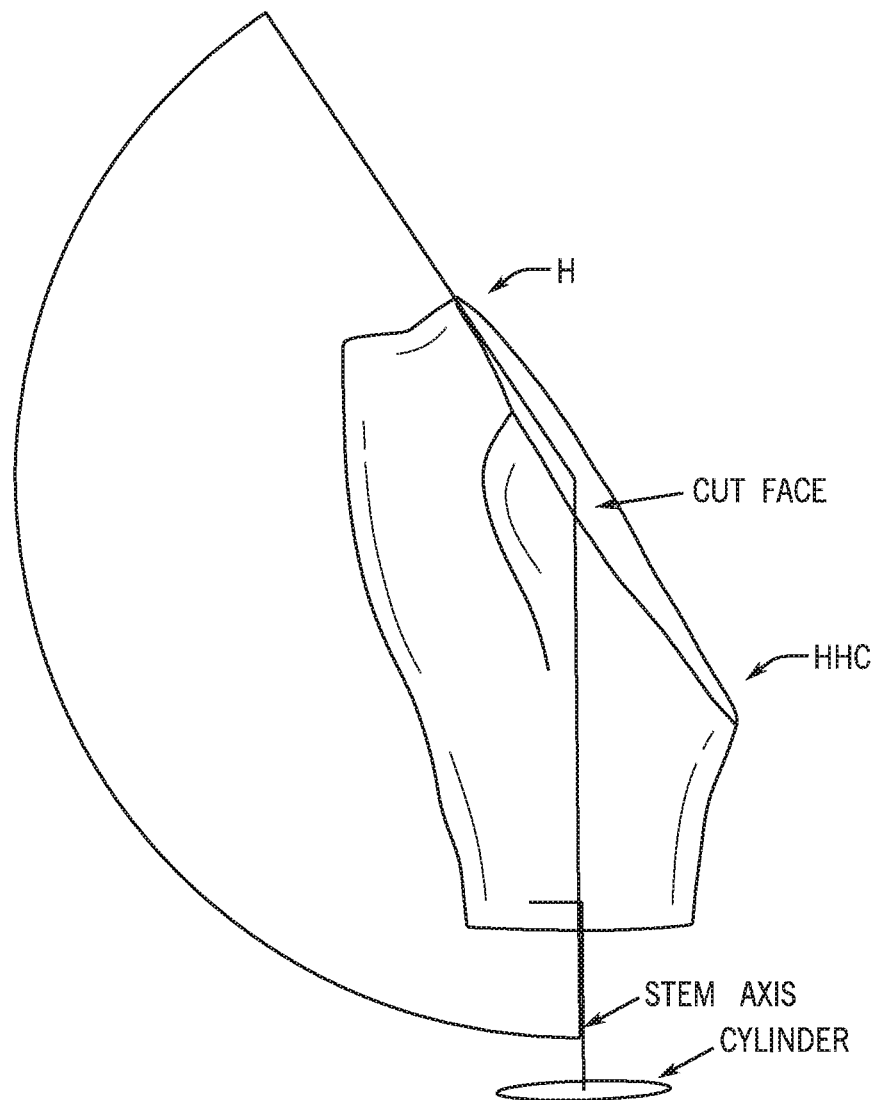
FIG. 19 is another image of the three dimensional model of a humerus created in accordance with the methodology of this disclosure. Reference lines and points are placed on the model.

In FIG. 19, reference lines and reference points were placed on the three dimensional model H. The humeral head cut inclination is measured in degrees. The humerus shaft is marked and this creates an axis through the center of the stem. Using the new axis and the vertical line from the anatomic cut face the angle can be measured. The inclination is 180-angle (shown in FIG. 19) plus 90. In this case, the inclination is 123 degrees)(180°−147°+90°.

Figure 20:
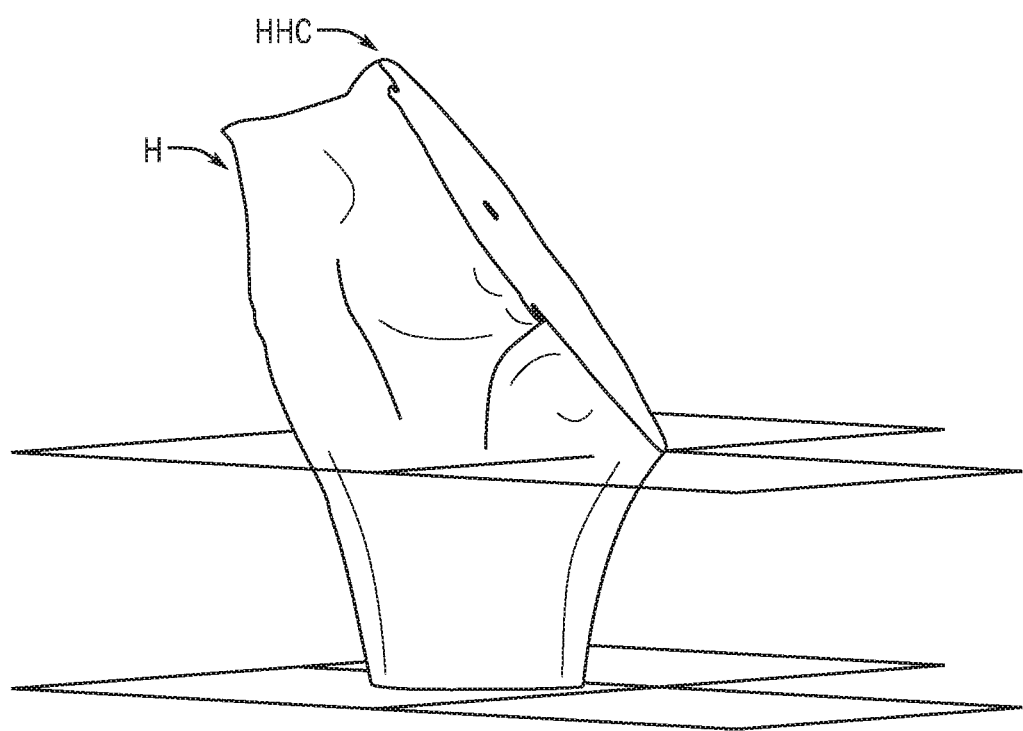
FIG. 20 is another image of the three dimensional model of a humerus created in accordance with the methodology of this disclosure. Reference lines and points are placed on the model.

In FIG. 20, reference planes were placed on the three dimensional model H. The top datum reference plane is perpendicular to the hollow cylinder created from FIG. 19 and the bottom datum plane is the cut plane. The cut reference plane is translated down 20 millimeters from the inferior aspect of the humeral head. Volume is calculated.

Figure 21:
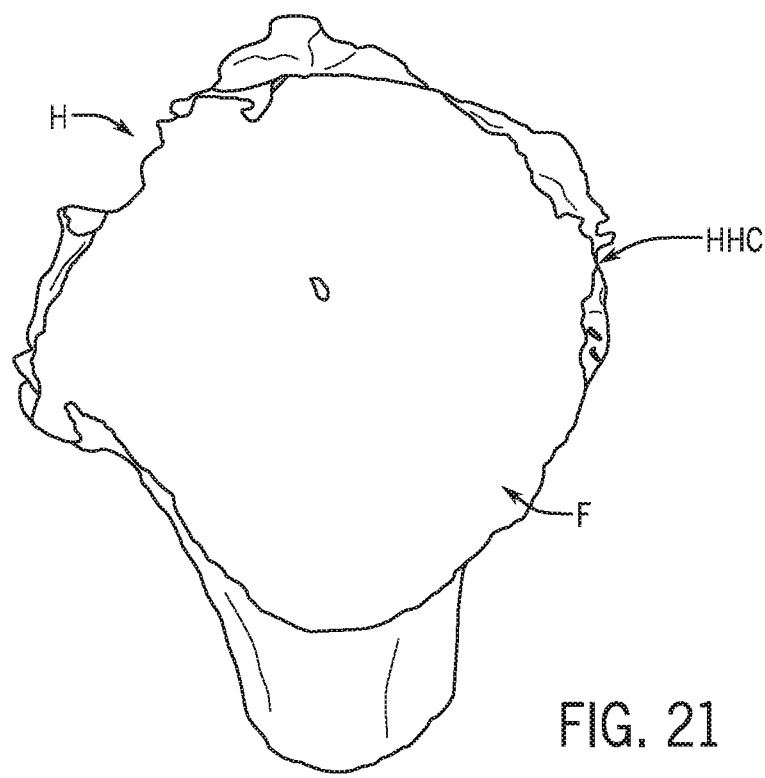
FIG. 21 is another image of the three dimensional model of a humerus created in accordance with the methodology of this disclosure. Reference lines and points are placed on the model.

In FIG. 21, the surface area of the anatomic humeral cut face F is calculated using the three dimensional model H.

Figure 22:
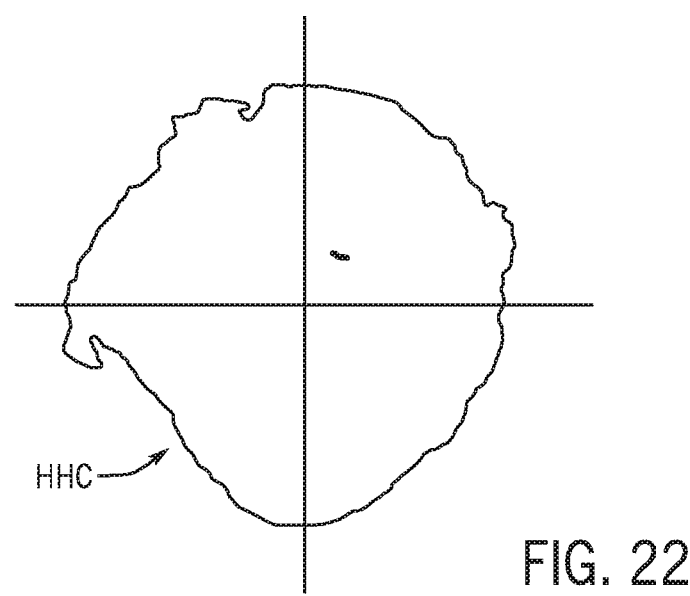
FIG. 22 is a screen shot of a humeral cut face of the three dimensional model of a humerus created in accordance with the methodology of this disclosure.

In FIG. 22, a screen shot of humeral cut face F of FIG. 21 allows for overlay of multiple samples. The sketches and contours are used for further shape analysis. For example, the method described herein may be performed upon a stack of contours or upon a stack of 3D virtual models taken from multiple patients for a particular size grouping. Patient size groups may be determined by particular characteristics, such as discussed below. In this example, the reference lines described below, or the depth measurement described above may be measured from a minimum size that would be available from such a patient group of stacked contours or 3D virtual models. A prosthetic designed from such a minimum size should fit all patients in a particular size group.

3. Humeral Head Cut Made 5 Millimeters Deeper than the Anatomic Cut

Looking at FIG. 23, reference planes were placed on the three dimensional model H. A five millimeter cut reference plane C5 is made by translating the anatomic humeral head cut reference plane HHC of FIG. 15 five millimeters deeper and parallel to the anatomic reference plane HHC. In some cases, surgeons have made a more aggressive cut to accommodate patients with rotator cuff insufficiency. Using the deeper than anatomic cut, C5 of FIG. 23, various measurements were made.

Figure 24:
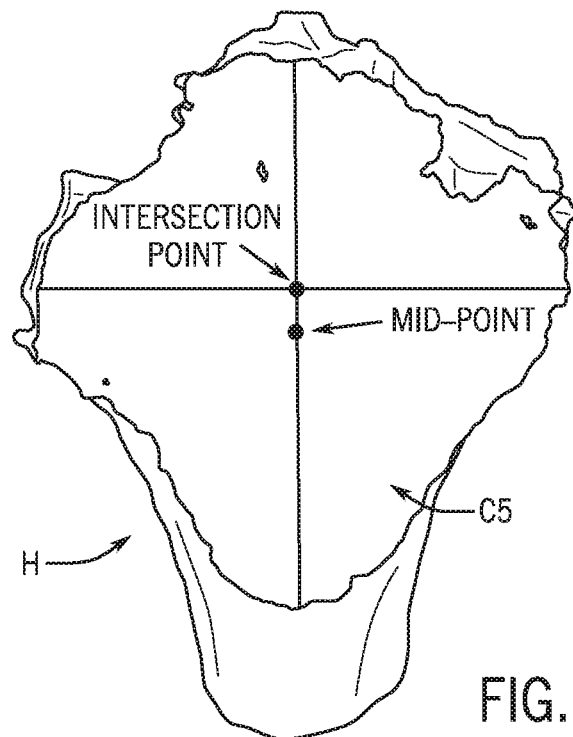
FIG. 24 is another image of the three dimensional model of a humerus created in accordance with the methodology of this disclosure. Reference lines and points are placed on the model.

In FIG. 24, reference lines and reference points were placed on the three dimensional model H. The vertical reference line was the greatest vertical distance on the cut face of humerus from the lowest point to highest point measured in millimeters. In FIG. 24, the horizontal reference line was the widest horizontal distance on the cut face of the humerus measured in millimeters. In FIG. 24, the mid-point was the reference point that is half of the vertical line. In FIG. 24, the intersection point is where the vertical and horizontal reference lines intersect.

Figure 25:
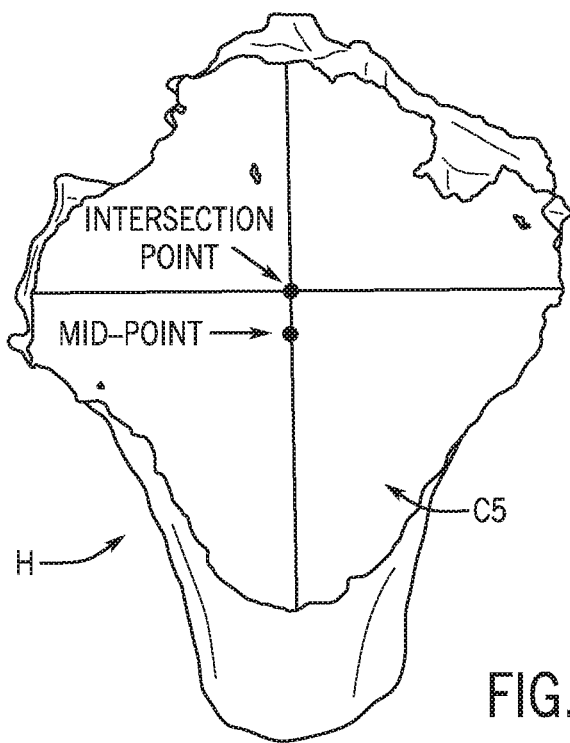
FIG. 25 is another image of the three dimensional model of a humerus created in accordance with the methodology of this disclosure. Reference lines and points are placed on the model.

In FIG. 25, reference lines and reference points were placed on the three dimensional model H. The delta is the distance measured from the mid-point to the intersection point in millimeters. Delta is positive when the intersection point is above the mid-point and negative when the intersection point is below the mid-point. In a perfect circle, these would overlap. Note the separation in delta between the five mm deeper cut C5 and the anatomic cut HHC, and the non-circular shape of the humerus.

Figure 26:
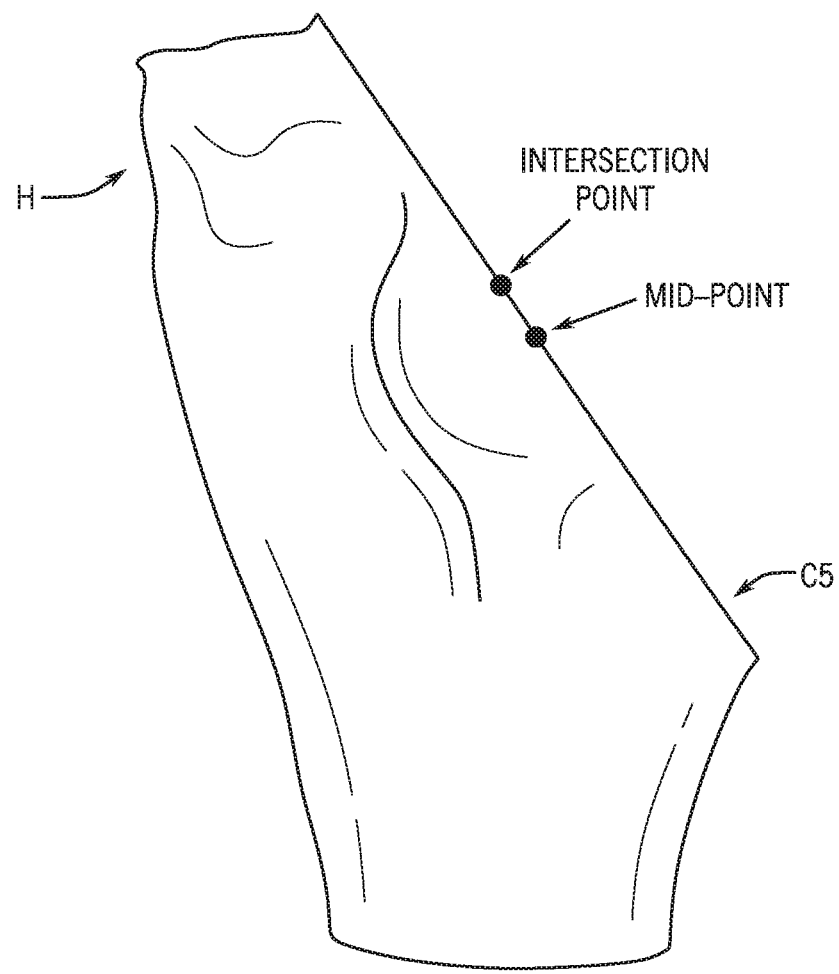
FIG. 26 is another image of the three dimensional model of a humerus created in accordance with the methodology of this disclosure. Reference lines and points are placed on the model.

In FIG. 26, reference lines and reference points were placed on the three dimensional model H. The depth from the mid-point (bottom line) is the depth from the mid-point to lateral edge of the humerus. This may depict the maximum depth of a humeral prosthetic component from this point. The depth from intersection point is the depth from intersection point (top line) to lateral edge of humerus. The maximum depth of a humeral prosthetic component may be from this point. Patients were ranked based on the depth of their remaining cancellous bone after a 5-mm cut, measured from the mid-point. After that ranking, the patients were then grouped, ten at a time into five total groups based upon depth. In the non-limiting embodiments of the stemless humeral component described above, we created five models that would fit the smallest in each of these groups and still occupy as much of the cancellous bone as possible to maximize stability.

In FIG. 27, reference planes were placed on the three dimensional model H. A reference plane is placed twenty millimeters below the inferior aspect of the humeral head cut HHC. The volume of the proximal humerus is calculated. There is a significant decrease in volume available in proximal humeral region.

Figure 28:
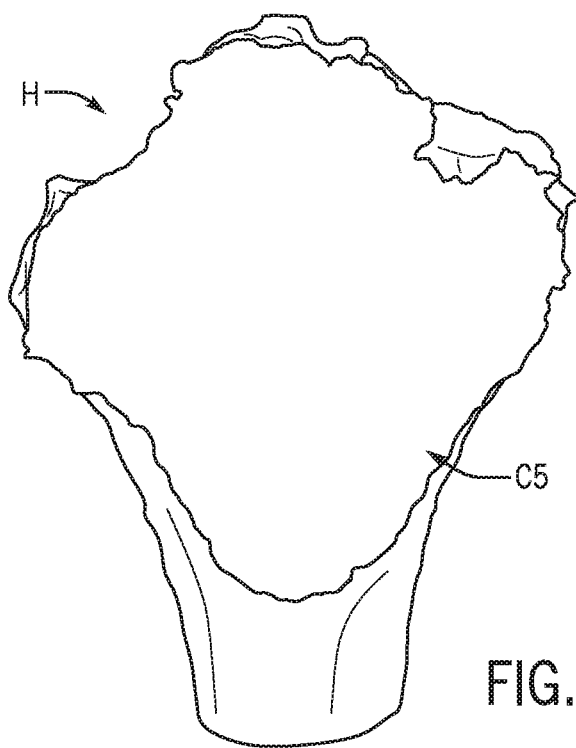
FIG. 28 is another image of the three dimensional model of a humerus created in accordance with the methodology of this disclosure. Reference lines and points are placed on the model.

In FIG. 28, the surface area of the deeper cut C5 versus the anatomic humeral cut HHC is calculated.

Figure 29:
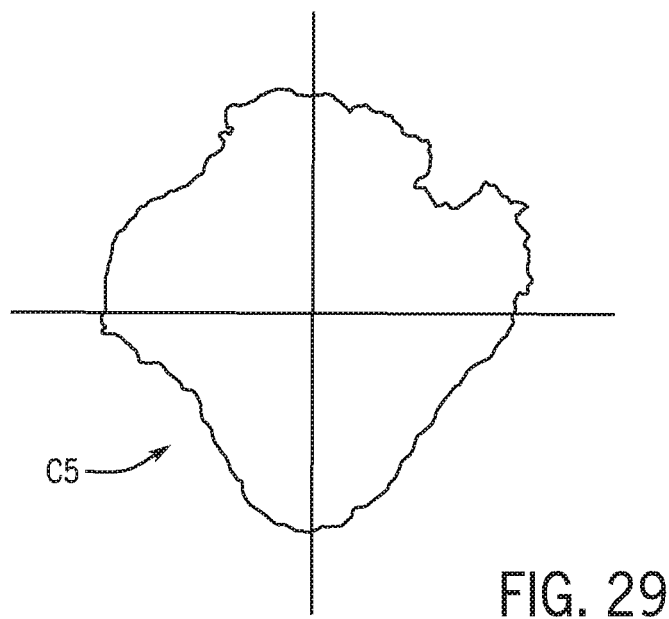
FIG. 29 is a screen shot of an alternative humeral cut face of the three dimensional model of a humerus created in accordance with the methodology of this disclosure.

In FIG. 29, a screen shot of the deeper cut C5 than anatomic humeral cut HHC allows for overlay of multiple samples. The sketches and contours are used for further shape analysis.

Figure 30:
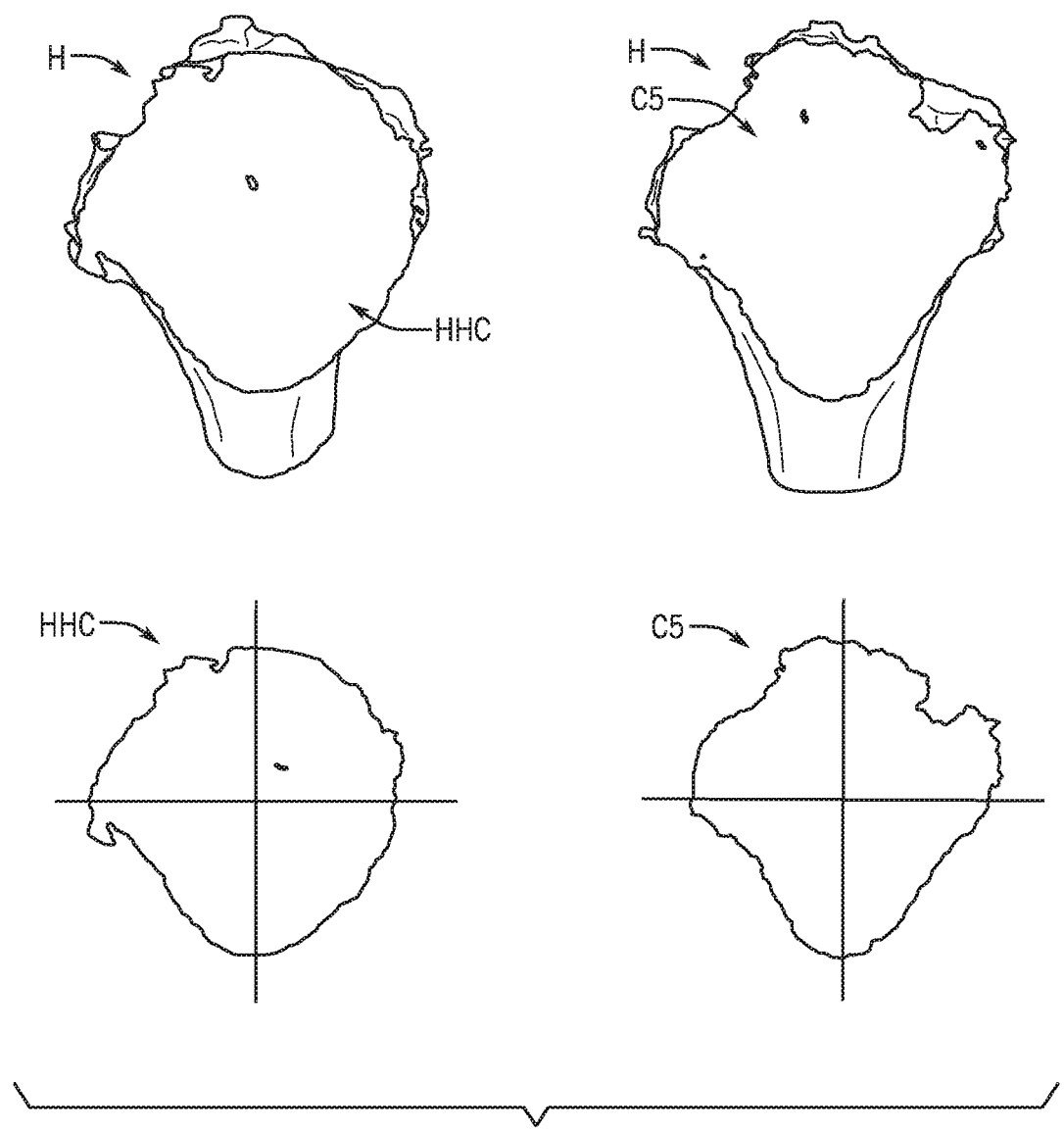
FIG. 30 shows side by side images of alternative humeral cut faces for the three dimensional model of a humerus created in accordance with the methodology of this disclosure. Side by side screen shots of the alternative humeral cut faces of the three dimensional model of a humerus created in accordance with the methodology of this disclosure are also shown.

FIG. 30 shows a comparison of the cut surface of the anatomic cut HHC and the deeper cut C5. One can see that the contour of the humerus is significantly different with the deeper cut C5 and is not round.

4. Greater and Lesser Tuberosity Measurements Made from Anatomic Cut

Figure 15:
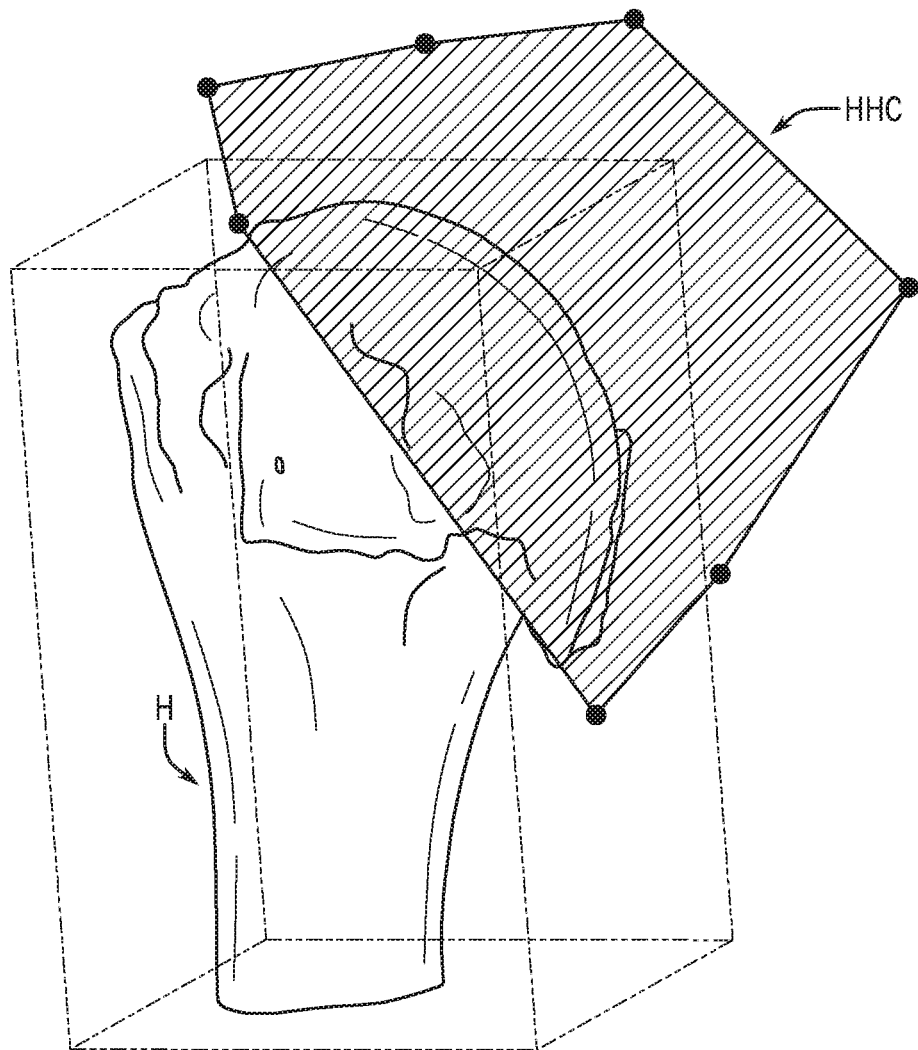
FIG. 15 is an image of a three dimensional model of a humerus created in accordance with the methodology of this disclosure using scans of the humerus. A bone cut reference plane is placed on the model.

Using the anatomic cut HHC of FIG. 15, various further reference measurements were made.

Figure 31:
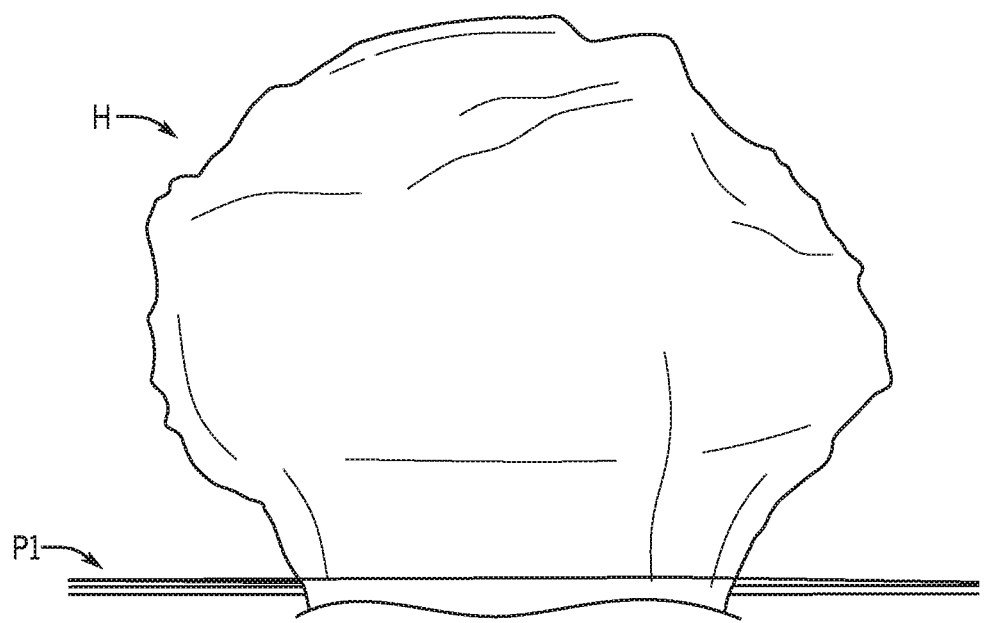
FIG. 31 is another image of the three dimensional model of a humerus created in accordance with the methodology of this disclosure. Reference lines and points are placed on the model.

In FIG. 31, the greater tuberosity width is the width of the greater tuberosity measured in millimeters, and the greater tuberosity height is the height of the greater tuberosity measured in millimeters stopping at a reference plane P1 defining the inferior aspect of the humeral head. The width is 30.26 millimeters and the height is 27.29 millimeters. The datum plane P1 on the inferior aspect is where all measurements were stopped to keep data consistent between varying sizes of anatomy.

Figure 32:
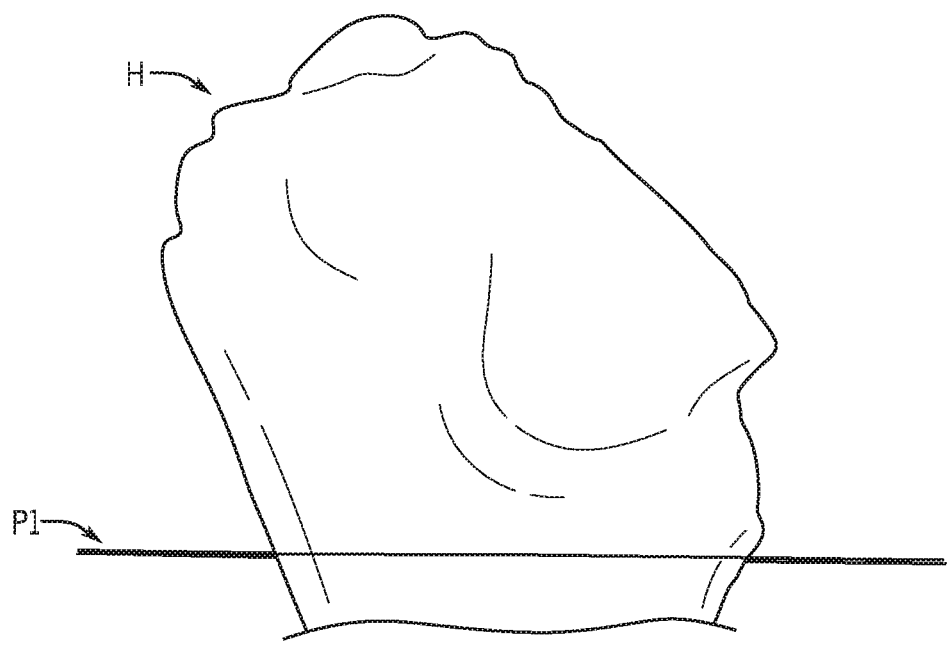
FIG. 32 is another image of the three dimensional model of a humerus created in accordance with the methodology of this disclosure. Reference lines and points are placed on the model.

In FIG. 32, the lesser tuberosity width is the width of the lesser tuberosity as measured in millimeters, and the lesser tuberosity height is the height of the lesser tuberosity as measured in millimeters.

Figure 33:
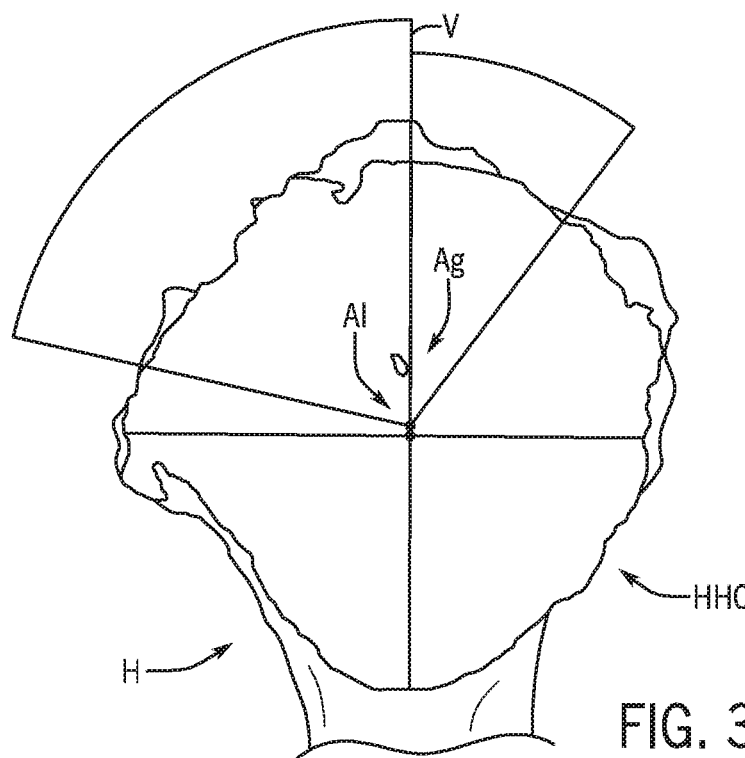
FIG. 33 is another image of the three dimensional model of a humerus created in accordance with the methodology of this disclosure. Reference lines and points are placed on the model.

FIG. 33 shows the reference angles to the greater and the lesser tuberosity mid-points on the cut surface contour. The greater tuberosity angle Ag was the angle from the mid-point of the greater tuberosity to the vertical line V in degrees (36.89° in FIG. 33). The lesser tuberosity angle Al was the angle from the mid-point of the lesser tuberosity to the vertical line V in degrees (77.79° in FIG. 33).

Figure 34:
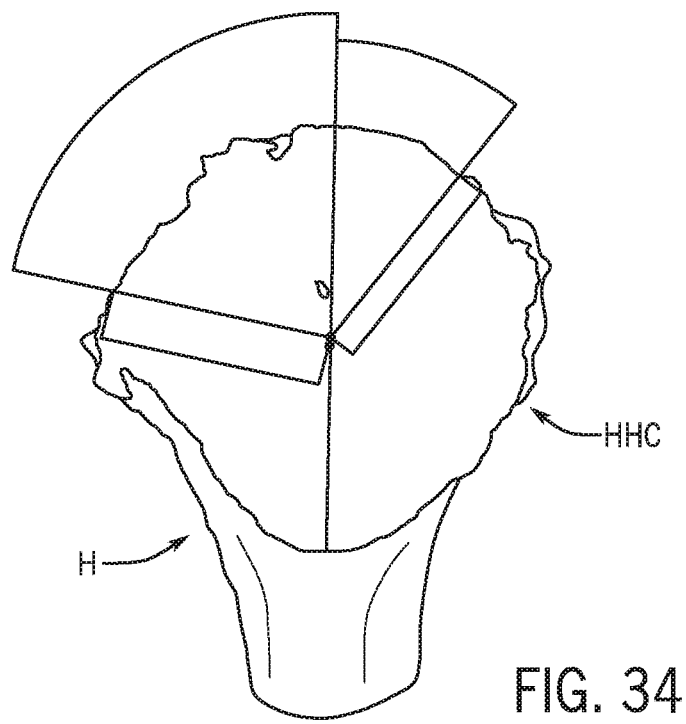
FIG. 34 is another image of the three dimensional model of a humerus created in accordance with the methodology of this disclosure. Reference lines and points are placed on the model.

FIG. 34 shows the distance from the mid-point to tuberosity mid-points on the cut face HHC. The distance from the mid-point of the humeral cut to the mid-point of the greater tuberosity was measured in millimeters (19.79 mm. in FIG. 33). The distance from the mid-point of the humeral cut to the mid-point of the lesser tuberosity was measured in millimeters (21.24 mm. in FIG. 33).

D. Results

Using the measurement methodology of this Example shown in FIGS. 15-34, a review was completed of fifty consecutive patients who had undergone anatomic shoulder arthroplasty. The following data was compiled.

The Patient Data was: Gender, Age at Surgery, Height, Weight, Anesthesia Time, Operative Time, Date of Last Exam, Date of Last Radiographs, Primary Operative Diagnosis, Secondary Diagnosis, Implant Type, Implant Size, Type of Fixation, Prior surgery, Complication, and Reoperation.

The CT Data statistics were presented as: Mean, standard deviation, median, minimum, maximum, 10th percentile and 90th percentile. See Table 1 below.

Ratios: In addition, the following ratios were obtained to gain a better understanding of the relationship of the proximal humeral anatomy:

vertical line distance/depth from midpoint;
horizontal line distance/depth from midpoint;
5 mm deeper cut vertical line distance/5 mm deeper cut depth at midpoint;
5 mm deeper cut horizontal line distance/5 mm deeper cut depth at midpoint;
greater tuberosity height/distance from midpoint to greater; and
lesser tuberosity height/distance from midpoint to lesser.
See Table 1 below.

TABLE 1

| | Mean | Standard Deviation | Median | Minimum | Maximum | 10th Percentile | 90th Percentile |
|---|---|---|---|---|---|---|---|
| Anatomic Humeral Cut | | | | | | | |
| Vertical line (mm) | 44.68 | 4.38 | 44.08 | 37.04 | 53.31 | 38.78 | 51.09 |
| Horizontal line (mm) | 43.3 | 4.2 | 42.41 | 32.67 | 54.47 | 39.15 | 49.05 |
| Mid-Point line (mm) | 22.73 | 3.74 | 22.04 | 18.52 | 43.79 | 19.39 | 25.99 |
| Delta (mm) | 2.34 | 2.32 | 2.76 | −2.43 | 7.93 | (−0.72) | 5.21 |
| Inclination (degrees) | 138.84 | 4.79 | 139.48 | 130.22 | 147.36 | 131.69 | 144.92 |
| Cortical head height (mm) | 24.22 | 2.95 | 24.22 | 18.36 | 32.3 | 20.09 | 28.08 |
| Depth from midpoint (mm) | 26.55 | 3.13 | 26.54 | 18.45 | 32.91 | 22.61 | 30.84 |
| Depth from intersection point (mm) | 25.8 | 3.09 | 26.09 | 18.49 | 32.74 | 22.23 | 29.75 |
| Volume (ml) | 31.363 | 7.754 | 32.337 | 16.904 | 46.139 | 20.971 | 41.623 |
| Surface area (mm²) | 1386.51 | 241.6 | 1389.97 | 922.83 | 1984.76 | 1068.72 | 1717.31 |
| 5 millimeter Deeper Humeral Cut | | | | | | | |
| Vertical line (mm) | 46.27 | 4.49 | 44.91 | 37.16 | 55.85 | 40.73 | 52.47 |
| Horizontal line (mm) | 43.12 | 4.84 | 43.18 | 27.38 | 51.37 | 37.53 | 49.52 |
| Mid-Point line (mm) | 23.21 | 2.25 | 22.35 | 18.58 | 27.92 | 20.37 | 26.24 |
| Delta (mm) | 3.21 | 2.32 | 2.75 | −1.37 | 8.95 | 0.73 | 6.31 |
| Depth from midpoint (mm) | 21.64 | 3 | 21.73 | 14.48 | 28.55 | 17.88 | 25.8 |
| Depth from intersection point (mm) | 20.55 | 2.88 | 20.71 | 12.54 | 26.11 | 17.08 | 24.39 |
| Volume (ml) | 24.498 | 6.659 | 25.351 | 11.660 | 38.280 | 15.640 | 33.038 |
| Surface area (mm²) | 1550.02 | 1245.45 | 1352.07 | 939.89 | 10013.62 | 1040.54 | 1747.13 |
| Tuberosity Measurements | | | | | | | |
| Greater tuberosity width (mm) | 33.54 | 3.79 | 34.08 | 25.42 | 43.26 | 27.82 | 37.85 |
| Greater tuberosity height (mm) | 30.18 | 4.95 | 29.31 | 13.01 | 41.2 | 25.15 | 36.06 |
| Lesser tuberosity width (mm) | 15.5 | 3.35 | 15.2 | 9.83 | 32.03 | 11.76 | 18.01 |
| Lesser tuberosity height (mm) | 24 | 3.52 | 23.97 | 15.5 | 32.02 | 19.62 | 29.38 |

TABLE 1-continued

| | | | | | | |
|---|---|---|---|---|---|---|
| Greater tuberosity angle (degrees) | 35.28 | 4.9 | 35.04 | 22.24 | 46.46 | 30.58 | 42.95 |
| Lesser tuberosity angle (degrees) | 69.96 | 6.13 | 68.75 | 58.29 | 83.52 | 62.37 | 77.89 |
| Distance from midpoint to greater tuberosity (mm) | 21.61 | 2.17 | 21.71 | 15.07 | 25.66 | 18.96 | 24.49 |
| Distance from midpoint to lesser tuberosity (mm) | 21.88 | 4.31 | 21.44 | 13.95 | 43.57 | 17.8 | 24.52 |

| | Mean | Standard Deviation | Median | Minimum | Maximum | 95% Confidence Intervals |
|---|---|---|---|---|---|---|
| Ratios | | | | | | |
| Ratios-Anatomic Humeral Cut | | | | | | |
| Vertical line distance/depth from midpoint | 1.6967 | 0.1842 | 1.7005 | 1.2656 | 2.13 | 1.65-1.175 |
| Horizontal line distance/depth from midpoint | 1.6455 | 0.1858 | 1.6619 | 1.2685 | 2.0495 | 1.59-1.7 |
| Ratios-Deeper Humeral Cut | | | | | | |
| Vertical line distance/depth from midpoint | 2.1731 | 0.3215 | 2.1868 | 1.4966 | 2.9965 | 2.08-2.26 |
| Horizontal line distance/depth from midpoint | 2.0265 | 0.2326 | 2.0605 | 1.5143 | 2.5664 | 1.96-2.09 |
| Ratios-Tuberosity Relationship | | | | | | |
| Greater tuberosity height/Distance from midpoint to greater tuberosity | 1.401 | 0.2048 | 1.4088 | 0.5548 | 1.7562 | 1.34-1.46 |
| Lesser tuberosity height/Distance from midpoint to lesser tuberosity | 1.1136 | 0.1517 | 1.1367 | 0.6142 | 1.3837 | 1.07-1.16 |

E. Proximal Humeral Anatomy

The methodology of this Example confirms that the proximal humerus is not circular in nature and clearly explains the challenges with forcing a circular or rectangular device in this region. The methodology revealed a specific pattern and shape of the proximal humeral region as noted in Table 1. One can see that the anatomic cut revealed a surface area that was not round. The deeper cut was even less round in shape. One can see that the depth of bone from the cut surface to the lateral cortex of the humerus decreases significantly with the deeper cut. This is further reflected in the ratio of the vertical line and horizontal line to the depth of bone available. Moreover, there is a substantial decrease in volume of bone available for fixation.

This method and 3D modeling identified specific anatomical patterns and facilitates developing devices that maximize contact with native bone and minimize risk of fracture. Moreover, the data from this methodology of this Example defines a specific range of anatomic sizes to accommodate patients.

F. Biomechanical Validation

A model was created to test the methodology of this Example. The model was based on the deeper cut due to the fact that less proximal bone is available and greater stress would be placed on the model-bone interface. The model can be modified to accommodate an anatomic cut or other potential applications.

The methodology resulted in a non-fracture model that is left and right side specific. There is a protrusion that is shaped to accommodate the mean angle and contour of the lesser tuberosity. The model revealed that two protrusions could be placed in the region of the greater tuberosity using the mean angle of the greater tuberosity as a reference point as well as the contour of the bone in this region as revealed by this methodology. See FIG. 2B. The three dimensional modeling also revealed a significant amount of bone on the inferior aspect of the proximal humerus that would improve stability. Additional protrusions were added to maximize bone contact based on the methodology. Five different size models were created based on the distribution of anatomic measurements and that optimized contact with underlying bone. See FIGS. 6A-6E. Each of the models was also made right and left specific.

Using three dimensional CT scans of a patient in the middle of the anatomic distribution, templating was performed to compare the maximum size commercially available circular device that could be placed compared to the maximum size anatomic model based on this novel methodology that could be placed in the proximal humeral bone.

A testing protocol was then created to quantify resistance to torque-out failure about the anterior-posterior axis of the anatomic model compared to a circular device. The anatomic model had both a grooved and ungrooved type. The grooved type was used to match the grooves on the commercially available device. Each model was implanted in a 60×60×40 mm piece of rigid polyurethane foam with density of 5 PCF (Pacific Research Laboratories, Inc., Vashon Island, Wash.), per the guidelines specified by ASTM F-1839-08 "Standard Specification for Rigid Polyurethane Foam for Use as a Standard Material for Testing Orthopaedic Devices and Instruments".

A cannulated technique was utilized. A guidewire was placed in the foam bone followed by drilling of a center hole. A preparation tool 2 millimeters in width was used to create channels for the 3 millimeters in width fins on the models. This allowed for a 1 millimeter interference fit when the model was placed in the foam. Each model was embedded to a depth such that the medial surface of the model was flush with the surface of the foam. A total of 6 models of each were tested.

Each embedded model was rigidly mounted to a 6-axis load cell (ATI Mini 58) via a bolt screwing into the central channel of the model such that the inferiorly located fin of the model pointed downward parallel to gravity. A torque replicating that of a shoulder-elevating motion was manually applied about the anterior-posterior axis until failure. Failure was defined as the model no longer being fixed within the block due to the foam fracturing around the model or the model sliding free of the foam. During this torque-out process, 3-axis force and 3-axis torque values were recorded at 100 Hz.

Figure 35:
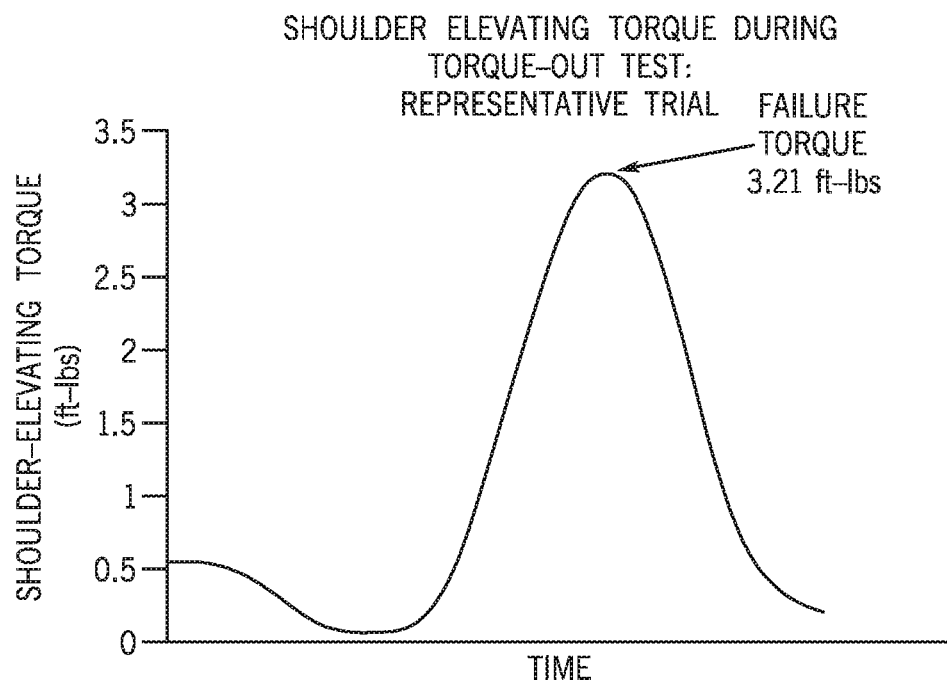
FIG. 35 is a graph of failure torque from a biomechanical validation study of non-limiting example stemless humeral component models produced in accordance with the methodology of this disclosure.
Figure 36:
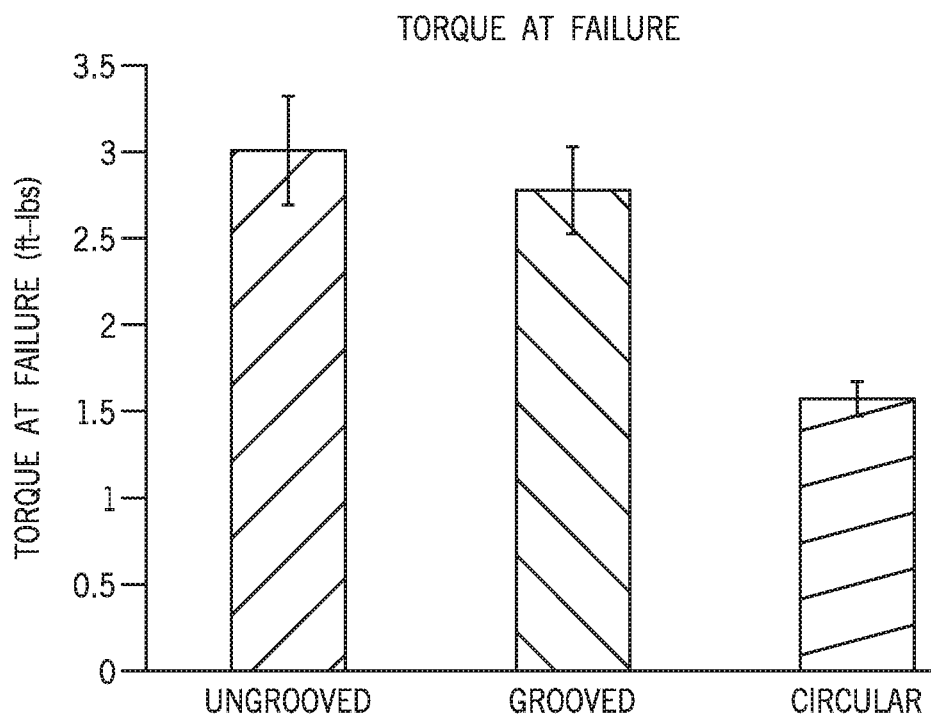
FIG. 36 is another graph of failure torque from a biomechanical validation study of non-limiting example stemless humeral component models produced in accordance with the methodology of this disclosure.

The resultant torque about the combined anterior-posterior and medio-lateral axes was computed for each trial. These combined torques represent the shoulder loads experienced during humeral elevation. Failure torque was defined as the peak torque during the test. A sample output from one model of the resultant torque with its peak value indicated is shown in FIG. 35, which is a representative trial of torque-out test showing the shoulder elevating torque (resultant torque about AP and ML axes) over time. The peak value is considered to be the failure torque and is labeled. The torque at failure for each of the three models, averaged across the six trials, is shown in FIG. 36. The anatomic and anatomic grooved models both had significantly greater resistance to torque-out failure than the circular model. The testing validated the methodology and demonstrated how anatomic features can be modified to distribute optimal loading and fit at the bone-device interface. Moreover, the maximum torque in the anatomic models was likely even higher due to the fact that in these cases the limiting factor was the foam bone breaking rather than sliding free of the bone as occurred with the circular model.

G. Fracture Model

A fracture model was also created based on the methodology of this Example and anatomic measurements. See FIGS. 9A-14. Five different size models were created based on the distribution of anatomic measurements and that optimized contact with underlying bone. Right and left specific models were created for each size. The size, shape, and location of fins to facilitate the accurate repair of the greater and lesser tuberosities was created. The fins being based on cancellous bone, rather than cortical bone further allows for anatomic reconstruction.

The greater tuberosity fin was placed at 35 degrees from the vertical axis. This was the mean angle determined by the methodology of this Example. The lesser tuberosity fin was placed at 70 degrees from the vertical axis. This was the mean angle determined by the methodology of this Example. Windows in the greater and lesser tuberosity fins also allow bone grafting and encourage healing. The modular nature of the invention also facilitates fine tune adjustment by allowing the surgeon to rotate the proximal body on the stem. In addition, models of a fluted, tapered short stem that could be used in a press fit manner were created.

The intent was to minimize the amount of metal in the implant to encourage bone to bone healing while still providing an anatomically correct scaffold to help guide and provide a secure repair of the greater and lesser tuberosities. The fin models were created with the same intent as the stemless implant—using the shape of real cancellous bone from patient scans to guide the fin shape. We decided on two fins that centered on the greater and lesser tuberosity to help guide the surgeon in repairing the fracture by providing anatomical markers. The position of the greater and lesser tuberosity fins were determined from the anatomical data acquired from the set of fifty patients. The average greater and lesser tuberosity angles were determined from the whole data set while, the size of the fins were optimized for each of the five category sizes to match the cancellous bone shape. The five category sizes for the fracture prosthesis were based upon the anatomic cut. Dimensions that were taken into account for the category sizes include, depth, contour surface of the anatomic cut, horizontal and vertical face sizes, surface area, volume, and location of the tuberosities. The lesser tuberosity fin also has a bend so that it can extend down toward the modular stem.

H. Cadaveric Validation

In addition to biomechanical testing, cadaveric validation of the models was performed.

I. Non-Fracture Model

A humeral head cut was made that is appropriate for a patient with arthritis and a rotator cuff tear. A template was used to determine the size of the model and a guidewire is placed. The cannulated reamer was used to create the center hole. The prep tool was then placed. After removing the prep tool, which may include treads to facilitate removal, the model was impacted in place. One has the ability to place a humeral head for hemiarthroplasty/anatomic shoulder arthroplasty or a tray for reverse arthroplasty on the model.

J. Fracture Model

The stem is fluted and tapered. Any proximal body can be used with any stem. In the fracture setting, the tuberosities were mobilized and the stem was press fit. One then matches the proximal humeral body to the patient's anatomy. The anatomic fin design with windows facilitates bone grafting and suture holes to facilitate repair. The model allows one to rotate the proximal body on the stem to fine tune the position of the fins. At the time of surgery, it can be challenging to determine the correct angular position of the tuberosities. If the tuberosities are rotated to far anterior or posterior, one can place the tuberosity fragments and associated rotator cuff under significant tension leading to failure. The anatomic position of the fins help guide the tuberosity repair to the correct orientation. One can use a humeral head for a hemiarthroplasty or humeral tray for a reverse arthroplasty with the model.

K. Applications of the Methodology

The development of the unique methodology of this Example can optimize the design of a wide spectrum of shoulder devices and offer a complete anatomic humeral offering. The methodology ensures that the product designs are correct the first time. By allowing for virtual design and validation, the methodology and database ensures the proper shaping and sizing of devices based on the true anatomy of patients undergoing these procedures. The methodology can improve the accuracy and efficiency of the design process, saving development cost and accelerating time to market. The methodology describes the interaction of anatomical features of the proximal humerus, describes how these features change based on the specific location in the humerus, and demonstrates that the shape is side specific. The methodology demonstrates that right and left specific devices with an anatomic shape in a true population based distribution may further facilitate and improve device design. This optimizes loading and fit at the bone-device interface.

1. Fracture Stem

The three dimensional proximal humeral anatomy that has been defined with the study of this Example also facilitates body design for proximal humerus fractures. This includes specific sizing of the fins used for fixing the greater and lesser tuberosities. A novel part of this method includes defining the angular relationship of the tuberosities in relation to each other. This allows the fracture stem fins to be designed with specific angles, height, and widths. These features assist and facilitate the anatomic repair of the tuberosities at the time of arthroplasty for fracture to improve bone healing and stability. One can also include the anatomic features into a tray design for reverse arthroplasty rather than a separate proximal body. The data and modeling of this Example indicate several possible options including the following.

a. Monoblock (One Piece Component)

One has the option of making a monoblock fracture stem with a proximal body that is proportionate to the stem diameter. This would allow a small proximal body with fins for smaller patients and large body with fins for a larger patient. Therefore, the implant becomes adaptable to the anatomy, rather than forcing the anatomy to adapt to the implant. These dimensions have an anatomic design based on the methodology of this Example.

b. Modular Proximal Body (Stem and Proximal Body are Separate Pieces)

This would be the first anatomic modular fracture stem to accommodate patients with different sizes of the tuberosities. The proximal body connects to the stem. This allows the surgeon to use the appropriate size proximal body for the patient.

c. Modular Fins

One could also have the option of having modular fins for suture attachment that could be connected to the proximal body/stem in varying locations. The fins can be available in variable sizes based on this method. One also has the option of modular body and fins.

d. Distal Aspect of the Stem

In addition to improvements in the proximal body, the distal aspect of the fracture stem could be improved with a tapered, non-rectangular geometry in 1 millimeter distal increments, extension of ingrowth material, and flutes for rotational control. This would facilitate use in an uncemented manner as well as use of a shorter stem. Additional design features to decrease stress shielding include the use of more flexible metal proximally such as titanium or foam metals such as tantalum. It may be possible to use a hollow stem to decrease stress shielding. Such a hollow stem may also be filled with a polymer material to improve stress distribution and thereby decrease stress shielding.

2. Humeral Fracture Fixation Devices

The methodology of this Example and the associated detailed understanding of the proximal humeral anatomy can facilitate design of improved fixation devices including intramedullary nails and plates. The methodology facilitates design of implants than can engage the best quality proximal humeral bone which is immediately below the cortex. In addition, the detailed understanding of the relationship of the tuberosities can improve the size, shape, and distribution of implants and angle that screws/blades/pegs could be placed. In addition, the specific angular relationship of the tuberosities defined by this methodology can direct anatomic fixation.

3. Proximal Humeral Replacement

There are numerous scenarios that may result in significant proximal humeral bone loss including revision shoulder replacement, trauma, and oncology reconstruction. Allograft bone reconstruction of missing humeral bone is susceptible to bone resorption. Current metallic product offerings are non-anatomic in shape resulting in implants that do not restore normal kinematics to the shoulder. The methodology of this Example facilitates the design of a complete anatomic proximal humeral bone replacement offering with correct sizes and shapes as well as the ability to design modular prostheses that use different materials for different components of the prosthesis.

4. Stemmed Shoulder Arthroplasty

The methodology of this Example also facilitates the design of a truly anatomic proximal portion of a humeral component in the appropriate size, shape, and size offerings. Stress shielding represents a significant problem and is reported in the literature. An anatomic proximal portion with uniform stress distribution would help decrease this problem. The methodology can also be used to facilitate the design of humeral heads, trays for reverse arthroplasty, as well as stems of varying lengths. As a non-limiting example, the length of a stem may be selected based upon specific pathoanatomy.

5. Resurfacing Arthroplasty

The methodology of this Example and associated detailed understanding of the proximal humeral architecture has the ability to maximize device contact with native bone, thereby minimizing stress shielding and gaining stability. The methodology also facilitates the design of a truly anatomic resurfacing arthroplasty in the appropriate size, shape, and size offerings.

6. Stemless Shoulder Arthroplasty

With reverse arthroplasty representing greater than 50% of the market for shoulder replacement, there is interest in expanding the use of stemless shoulder arthroplasty to reverse arthroplasty in the United States. However, there have been reports of higher failure in Europe when stemless is used with reverse. The more constrained nature of the reverse design along with greater risk of impingement at the end range of motion places increased stress on the implant.

Due to the increased stress on the stemless design with reverse arthroplasty, some surgeons have attempted to place the component in contact with the harder cortical bone in an attempt to gain stability. In addition, there is a desire to place a larger size stemless device to maximize contact with the best bone which is in the cortical region. This has resulted in some surgeons fracturing the cortical bone or placing an implant that penetrates the cortical bone creating a substantial risk of a stress riser with increased risk of future fracture and failure of the prosthesis.

In order to have an implant that maximizes contact with the best quality humeral bone, one needs an implant that matches the proximal humeral anatomy. All of the current stemless designs in the market are circular in nature and not side specific. As the methodology clearly demonstrates, the proximal humeral region is not circular, particularly when a reverse arthroplasty is performed. The humeral cut with a reverse is typically 5 millimeters more distal than an anatomic humeral cut, particularly with an onlay design. Therefore, the proximal humeral shape and size is different for a reverse compared to an anatomic arthroplasty. This was confirmed in the methodology of this Example and has the potential to impact implant design.

Therefore, forcing a circular implant into non-circular bone increases the risk of fracture and fails to maximize contact with the best quality humeral bone. Therefore, the ideal stemless or humeral stem design should be based on the true shape of the proximal humerus. In addition, the distribution of implant sizes available should be based on a true anatomic distribution. An additional aspect includes the concept that shape of the proximal humeral region may be side specific. Therefore, having right and left specific implants with an anatomic shape in a true population based distribution may further improve shoulder arthroplasty design. The methodology facilitates the design of an anatomic stemless device with improved shape, size, and fit.

7. Minimally Invasive Shoulder Solutions

There has been a significant drive to less invasive procedures minimizing bone removal. The methodology of this Example and associated detailed understanding of the proximal humerus has the ability to facilitate the design of less invasive procedures while maximizing device stability in the proximal humeral region.

8. Other Applications

This study of this Example and resultant methodology was performed to further define the proximal humeral shape and size distribution. It is also evident that implants based on the true anatomy and the described methodology would be beneficial in other areas including hip, knee, ankle, elbow, wrist, hand, and spine.

Thus, this methodology provides for the ability to design stemless components and fracture stems for joint arthroplasty, such as shoulder arthroplasty, and methods for the optimization of joint arthroplasty component design.

For any of these applications, a patient specific, custom designed prosthesis may be built based upon image data and the methodology described above for the patient in question. In this way, the prosthetic may be created specifically for the patient using additive manufacturing, or a 3D printer capable of creating a prosthetic out of the required materials, such as cobalt chrome, titanium, stainless steel, or other metals, plastics, ceramics, and the like. If multiple materials are needed to build different components of a modular prosthesis, different 3D printers or other manufacturing methods may be used to make different parts that are then assembled for final implantation into the patient. A number of non-limiting examples of manufacturing techniques such as milling, molding, additive manufacturing, and others can be used as manufacturing systems that could be deployed for building the patient specific devices described above.

The methodology enables the ability to design patient specific asymmetric implants, such as stemless, stemmed, fracture devices, or proximal humeral replacements, where the surgeon has the ability to preoperatively determine the optimal size, shape, and orientation for a feature, such as a fin/wing/protrusion/body, of an implant for a specific patient. The implant can be custom made for an individual patent with custom instrumentation to facilitate intraoperative bone preparation and implantation.

The methodology may be further modified to include an automated process of implant component design where such an automated routine performs measurements automatically on a medical image and optimized implant design features that may be patient specific, or may be used to indicate which size device would be optimally suited for a patient." Automated or manually, the methodology (such as by measuring proximal humeral depth from the humeral cut) determines the optimal implant, either custom or stock implant, to be selected and ultimately implanted in a patient.

Although what has been described in detail here is with reference to certain embodiments, one skilled in the art will appreciate that the present invention can be practiced by someone other than with the described embodiments, which have been presented for purposes of illustration and not of limitation. Therefore, the scope of the appended claims should not be limited to the description of the embodiments contained herein.

What is claimed is:

1. A prosthesis comprising:
a central body having a longitudinal axis normal to a reference plane that extends through the central body;
at least five fins extending laterally from an outer surface of the central body, the at least five fins being spaced apart around the outer surface of the central body,
a first fin of the at least five fins configured to align when implanted with a lesser tuberosity of a humerus of a subject;
a second fin of the at least five fins configured to align when implanted with a greater tuberosity of the humerus of the subject;
a third fin of the at least five fins disposed between the first fin and the second fin;
wherein spacing of the at least five fins is asymmetric in the reference plane.

2. The prosthesis of claim 1, wherein the at least five fins do not create bilateral symmetry of the at least five fins with respect to a longitudinal plane containing the longitudinal axis due to the spacing in the reference plane of the at least five fins.

3. The prosthesis of claim 1, further comprising a sixth fin to form at least six fins extending laterally from the outer surface of the central body, the at least six fins being spaced apart around the outer surface of the central body, and
wherein spacing of the at least six fins is asymmetric in the reference plane.

4. The prosthesis of claim 1, wherein the central body has a first opening and a second opening, the first opening corresponding to a proximal side of the central body and the second opening corresponding to a distal side of the central body.

5. The prosthesis of claim 1, wherein at least one of the at least five fins has an inner perimeter and an outer perimeter, the inner perimeter and the central body defining at least one window, at least one of the at least five fins having the at least one window includes one or more throughholes in a wall defined by the inner perimeter and the outer perimeter of the at least one of the at least five fins having the at least one window.

6. The prosthesis of claim 1, further comprising
a first section having a first articular surface dimensioned to articulate with a second articular surface of a native bone or a prosthetic component; and a coupler connected to the central body, the coupler being dimensioned to be connected to the central body,
wherein the first articular surface is convex.

7. The prosthesis of claim 1, further comprising
a first section having a first articular surface dimensioned to articulate with a second articular surface of a native bone or a prosthetic component; and a coupler connected to the central body, the coupler being dimensioned to be connected to the central body,
wherein the first articular surface is concave.

8. A prosthesis comprising:
a central body having a longitudinal axis normal to a reference plane that extends through the central body;
a plurality of fins extending laterally from an outer surface of the central body, the plurality of fins being spaced apart around the outer surface of the central body,
wherein spacing of the plurality of fins is asymmetric in the reference plane,
wherein all of the plurality of fins do not create bilateral symmetry of all of the plurality of fins with respect to a longitudinal plane containing the longitudinal axis due to the spacing in the reference plane of the plurality of fins, and
wherein a first fin of the plurality of fins aligns when implanted with a lesser tuberosity of a humerus of a subject at an angle ranging from 58.29 degrees up to and including 83.52 degrees from a vertical axis of the prosthesis,
wherein a second fin of the plurality of fins aligns with a greater tuberosity of the humerus when the prosthesis is implanted in the humerus, and
wherein the second fin has a length ranging from 15.07 mm up to and including 25.66 mm.

9. The prosthesis of claim 8, wherein the second fin is aligned when implanted with the greater tuberosity at an angle ranging from 22.24 degrees up to and including 46.46 degrees from the vertical axis of the prosthesis.

10. The prosthesis of claim 8, wherein the first fin has a length ranging from 13.95 mm up to and including 43.57 mm.

11. The prosthesis of claim 8, wherein the plurality of fins includes at least five fins, wherein spacing of the five fins is asymmetric in the reference plane.

12. The prosthesis of claim 8, wherein the plurality of fins includes at least six fins, wherein spacing of the six fins is asymmetric in the reference plane.

13. The prosthesis of claim 8, further comprising an inferior fin of the plurality of fins that aligns with an inferior position of the humerus when the prosthesis is implanted in the humerus.

14. The prosthesis of claim 8, further comprising an accessory fin of the plurality of fins that aligns with a posterior-inferior position of the humerus to capture posterior-inferior bone when the prosthesis is implanted in the humerus.

15. The prosthesis of claim 8, further comprising
a first section having a first articular surface dimensioned to articulate with a second articular surface of a native bone or a prosthetic component; and a coupler connected to the central body, the coupler being dimensioned to be connected to the central body,
wherein the first articular surface is convex.

16. The prosthesis of claim 8, further comprising
a first section having a first articular surface dimensioned to articulate with a second articular surface of a native bone or a prosthetic component; and a coupler connected to the central body, the coupler being dimensioned to be connected to the central body,
wherein the first articular surface is concave.

17. A prosthesis comprising:
a central body having a longitudinal axis normal to a reference plane that extends through the central body and dimensioned for implantation into a humerus of a subject;
a plurality of fins extending laterally from an outer surface of the central body, the plurality of fins being spaced apart around the outer surface of the central body and dimensioned for implantation into the humerus of the subject,
a first fin of the plurality of fins configured to align when implanted with a lesser tuberosity of the humerus of the subject;
a second fin of the plurality fins configured to align when implanted with a greater tuberosity of the humerus of the subject;
a third fin of the plurality of fins disposed between the first fin and the second fin;
wherein spacing of the plurality of fins is asymmetric in the reference plane,
wherein all of the plurality of fins do not create bilateral symmetry of all of the plurality of fins with respect to a longitudinal plane containing the longitudinal axis due to the spacing in the reference plane of the plurality of fins.

18. The prosthesis of claim 17 wherein:
a first fin of the plurality of fins has a first fin length, the first fin length defined by a first distance from the central body to an outermost radial edge of the first fin,
a second fin of the plurality of fins has a second fin length, the second fin length defined by a second distance from the central body to an outermost radial edge of the second fin,
wherein the second fin length is less than the first fin length.

19. The prosthesis of claim 17, wherein the central body has a first opening and a second opening, the first opening corresponding to a proximal side of the central body and the second opening corresponding to a distal side of the central body.

20. The prosthesis of claim 17, wherein at least one of the plurality of fins is modular and removeably coupled to the central body.

21. The prosthesis of claim 17, further comprising
a first section having a first articular surface dimensioned to articulate with a second articular surface of a native bone or a prosthetic component; and a coupler connected to the central body, the coupler being dimensioned to be connected to the central body,
wherein the first articular surface is convex.

22. The prosthesis of claim 17, further comprising
a first section having a first articular surface dimensioned to articulate with a second articular surface of a native bone or a prosthetic component; and a coupler connected to the central body, the coupler being dimensioned to be connected to the central body,
wherein the first articular surface is concave.

23. The prosthesis of claim 17, wherein at least one of the plurality of fins has an inner perimeter and an outer perimeter, the inner perimeter and the central body defining at least one window, at least one of the fins having the at least one window includes one or more throughholes in a wall defined by the inner perimeter and the outer perimeter of the fin having the at least one window.

* * * * *

UNITED STATES PATENT AND TRADEMARK OFFICE
CERTIFICATE OF CORRECTION

PATENT NO. : 11,612,489 B2  
APPLICATION NO. : 17/489335  
DATED : March 28, 2023  
INVENTOR(S) : John W. Sperling Page 1 of 1

It is certified that error appears in the above-identified patent and that said Letters Patent is hereby corrected as shown below:

In the Specification

Column 12, Line 10, "1000" should be --100G--.

Column 12, Line 12, "1000" should be --100G--.

Column 12, Line 13, "1000" should be --100G--.

Column 13, Line 14, "1000" should be --100G--.

Column 18, Line 7, "2000" should be --200G--.

Column 21, Line 61, "degrees)(180°-147°+90°." should be --degrees (180°-147°+90°).--.

Signed and Sealed this  
Thirtieth Day of May, 2023

Katherine Kelly Vidal  
*Director of the United States Patent and Trademark Office*